(12) United States Patent
Glithero et al.

(10) Patent No.: US 11,529,252 B2
(45) Date of Patent: Dec. 20, 2022

(54) FLUID COLLECTION GARMENTS

(71) Applicant: PUREWICK CORPORATION, El Cajon, CA (US)

(72) Inventors: Jason Iain Glithero, McDonough, GA (US); Ashley Marie Johannes, Atlanta, GA (US); Tracey Knapp, Snellville, GA (US); Andrew Meyer, Atlanta, GA (US); David Mornhinweg, Watkinsville, GA (US)

(73) Assignee: PureWick Corporation, El Cajon, CA (US)

( * ) Notice: Subject to any disclaimer, the term of this patent is extended or adjusted under 35 U.S.C. 154(b) by 0 days.

(21) Appl. No.: 16/905,400

(22) Filed: Jun. 18, 2020

(65) Prior Publication Data

US 2020/0390591 A1 Dec. 17, 2020

Related U.S. Application Data

(63) Continuation of application No. PCT/US2019/029613, filed on Apr. 29, 2019.

(60) Provisional application No. 62/665,335, filed on May 1, 2018.

(51) Int. Cl.
*A61F 5/44* (2006.01)
*A61F 5/455* (2006.01)
*A61F 5/453* (2006.01)
*A61M 1/00* (2006.01)

(52) U.S. Cl.
CPC .......... *A61F 5/4408* (2013.01); *A61F 5/4401* (2013.01); *A61F 5/453* (2013.01); *A61F 5/455* (2013.01); *A61M 1/0023* (2013.01)

(58) Field of Classification Search
CPC ...... A61F 5/4408; A61F 5/4401; A61F 5/453; A61F 5/455; A61M 1/0023
See application file for complete search history.

(56) References Cited

U.S. PATENT DOCUMENTS

| | | | |
|---|---|---|---|
| 670,602 | A | 3/1901 | Baker |
| 1,032,841 | A | 7/1912 | Koenig |
| 1,742,080 | A | 12/1929 | Jones |

(Continued)

FOREIGN PATENT DOCUMENTS

| | | |
|---|---|---|
| CA | 2165286 C | 9/1999 |
| CA | 2354132 A1 | 6/2000 |

(Continued)

OTHER PUBLICATIONS

US 9,908,683 B2, 03/2018, Sandhausen et al. (withdrawn)

(Continued)

*Primary Examiner* — Guy K Townsend
(74) *Attorney, Agent, or Firm* — Dorsey & Whitney LLP

(57) ABSTRACT

Examples relate to garments, systems, and methods for fluid collection or removing fluids from a fluid collection device. The fluid collection garments include a fabric body configured to be worn on the pelvis of a wearer, where the fabric body has a port thereon or therein, where the port holds a fluid collection device therein. The fluid collection device is shaped to complement the female anatomy or male anatomy near the urethra. The fluid collection device can include a vacuum source in fluid communication with the fluid collection device via one or more sections of conduit.

20 Claims, 8 Drawing Sheets

(56) References Cited

U.S. PATENT DOCUMENTS

| | | | |
|---|---|---|---|
| 1,979,899 A | 11/1934 | Obrien et al. | |
| 2,326,881 A | 8/1943 | Packer | |
| 2,613,670 A | 10/1952 | Edward | |
| 2,644,234 A | 7/1953 | Earl | |
| 2,859,786 A | 11/1958 | Tupper | |
| 2,968,046 A * | 1/1961 | Duke | A61G 9/006 604/149 |
| 2,971,512 A | 2/1961 | Reinhardt | |
| 3,032,038 A | 5/1962 | Swinn | |
| 3,087,938 A | 4/1963 | Hans et al. | |
| 3,198,994 A | 8/1965 | Hildebrandt et al. | |
| 3,221,742 A | 12/1965 | Egon | |
| 3,312,981 A | 4/1967 | Mcguire et al. | |
| 3,349,768 A | 10/1967 | Keane | |
| 3,362,590 A | 1/1968 | Gene | |
| 3,366,116 A | 1/1968 | Huck | |
| 3,398,848 A | 8/1968 | Donovan | |
| 3,400,717 A | 9/1968 | Bruce et al. | |
| 3,406,688 A | 10/1968 | Bruce | |
| 3,425,471 A | 2/1969 | Yates | |
| 3,511,241 A | 5/1970 | Lee | |
| 3,512,185 A | 5/1970 | Ellis | |
| 3,520,300 A | 7/1970 | Flower | |
| 3,528,423 A | 9/1970 | Lee | |
| 3,613,123 A | 10/1971 | Langstrom | |
| 3,651,810 A | 3/1972 | Ormerod | |
| 3,699,815 A | 10/1972 | Holbrook | |
| 3,726,277 A | 4/1973 | Hirschman | |
| 3,843,016 A | 10/1974 | Bornhorst et al. | |
| 3,863,798 A | 2/1975 | Kurihara et al. | |
| 3,915,189 A | 10/1975 | Holbrook et al. | |
| 3,998,228 A | 12/1976 | Poidomani | |
| 3,999,550 A | 12/1976 | Martin | |
| 4,015,604 A | 4/1977 | Csillag | |
| 4,020,843 A | 5/1977 | Kanall | |
| 4,022,213 A | 5/1977 | Stein | |
| 4,027,776 A | 6/1977 | Douglas | |
| 4,180,178 A | 12/1979 | Turner | |
| 4,187,953 A | 2/1980 | Turner | |
| 4,194,508 A | 3/1980 | Anderson | |
| 4,200,102 A * | 4/1980 | Duhamel | A61F 5/451 604/353 |
| 4,202,058 A | 5/1980 | Anderson | |
| 4,233,025 A | 11/1980 | Larson et al. | |
| 4,233,978 A | 11/1980 | Hickey | |
| 4,246,901 A | 1/1981 | Frosch et al. | |
| 4,257,418 A | 3/1981 | Hessner | |
| 4,270,539 A * | 6/1981 | Frosch | A61F 5/455 604/347 |
| 4,292,916 A | 10/1981 | Bradley et al. | |
| 4,352,356 A | 10/1982 | Tong | |
| 4,360,933 A | 11/1982 | Kimura et al. | |
| 4,365,363 A | 12/1982 | Windauer | |
| 4,387,726 A | 6/1983 | Denard | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,476,879 A | 10/1984 | Jackson | |
| 4,526,688 A | 7/1985 | Schmidt et al. | |
| 4,528,703 A | 7/1985 | Kraus | |
| D280,438 S | 9/1985 | Wendt | |
| 4,553,968 A | 11/1985 | Komis | |
| 4,581,026 A | 4/1986 | Schneider | |
| 4,610,675 A | 9/1986 | Triunfol | |
| 4,626,250 A | 12/1986 | Schneider | |
| 4,627,846 A | 12/1986 | Ternstroem | |
| 4,631,061 A * | 12/1986 | Martin | A61F 5/451 604/323 |
| 4,650,477 A | 3/1987 | Johnson | |
| 4,656,675 A | 4/1987 | Fajnsztajn | |
| 4,681,570 A | 7/1987 | Dalton | |
| 4,692,160 A | 9/1987 | Nussbaumer | |
| 4,707,864 A | 11/1987 | Ikematsu et al. | |
| 4,713,066 A | 12/1987 | Komis | |
| 4,747,166 A * | 5/1988 | Kuntz | A61F 5/455 4/144.1 |
| 4,752,944 A | 6/1988 | Conrads et al. | |
| 4,769,215 A | 9/1988 | Ehrenkranz | |
| 4,772,280 A | 9/1988 | Rooyakkers | |
| 4,790,830 A | 12/1988 | Hamacher | |
| 4,790,835 A | 12/1988 | Elias | |
| 4,791,686 A | 12/1988 | Taniguchi et al. | |
| 4,795,449 A | 1/1989 | Schneider et al. | |
| 4,799,928 A | 1/1989 | Crowley | |
| 4,804,377 A | 2/1989 | Hanifl et al. | |
| 4,812,053 A | 3/1989 | Bhattacharjee | |
| 4,820,297 A | 4/1989 | Kaufman et al. | |
| 4,846,818 A | 7/1989 | Keldahl et al. | |
| 4,846,909 A | 7/1989 | Klug et al. | |
| 4,865,595 A | 9/1989 | Heyden | |
| 4,882,794 A | 11/1989 | Stewart, III | |
| 4,883,465 A | 11/1989 | Brennan | |
| 4,886,508 A * | 12/1989 | Washington | A61F 5/455 604/347 |
| 4,886,509 A | 12/1989 | Mattsson | |
| 4,889,533 A | 12/1989 | Beecher | |
| 4,903,254 A | 2/1990 | Haas | |
| 4,905,692 A | 3/1990 | More | |
| 4,955,922 A | 9/1990 | Terauchi | |
| 4,965,460 A | 10/1990 | Tanaka et al. | |
| 4,987,849 A | 1/1991 | Sherman | |
| 5,002,541 A | 3/1991 | Conkling et al. | |
| 5,004,463 A | 4/1991 | Nigay | |
| 5,031,248 A | 7/1991 | Kemper | |
| 5,045,077 A | 9/1991 | Blake | |
| 5,045,283 A | 9/1991 | Patel | |
| 5,049,144 A * | 9/1991 | Payton | A61F 5/455 600/574 |
| 5,053,339 A | 10/1991 | Patel | |
| 5,058,088 A | 10/1991 | Haas et al. | |
| 5,071,347 A | 12/1991 | Mcguire | |
| 5,084,037 A | 1/1992 | Barnett | |
| 5,100,396 A | 3/1992 | Zamierowski | |
| 5,147,301 A | 9/1992 | Ruvio | |
| 5,195,997 A | 3/1993 | Carns | |
| 5,203,699 A | 4/1993 | Mcguire | |
| 5,244,458 A | 9/1993 | Takasu | |
| 5,267,988 A | 12/1993 | Farkas | |
| 5,275,307 A | 1/1994 | Freese | |
| 5,294,983 A | 3/1994 | Ersoz et al. | |
| 5,295,983 A | 3/1994 | Kubo | |
| 5,300,052 A | 4/1994 | Kubo | |
| 5,382,244 A | 1/1995 | Telang | |
| 5,423,784 A | 6/1995 | Metz | |
| 5,466,229 A * | 11/1995 | Elson | A61M 1/0023 604/323 |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,618,277 A | 4/1997 | Goulter | |
| 5,628,735 A | 5/1997 | Skow | |
| 5,636,643 A | 6/1997 | Argenta et al. | |
| 5,637,104 A | 6/1997 | Ball et al. | |
| 5,674,212 A * | 10/1997 | Osborn, III | A61F 13/15 604/385.16 |
| 5,678,564 A * | 10/1997 | Lawrence | A61F 5/455 600/573 |
| 5,678,654 A | 10/1997 | Uzawa | |
| 5,687,429 A | 11/1997 | Rahlff | |
| 5,695,485 A | 12/1997 | Duperret et al. | |
| 5,752,944 A | 5/1998 | Dann et al. | |
| 5,772,644 A | 6/1998 | Bark et al. | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,865,378 A | 2/1999 | Hollinshead et al. | |
| 5,887,291 A | 3/1999 | Bellizzi | |
| 5,894,608 A | 4/1999 | Birbara | |
| D409,303 S | 5/1999 | Oepping | |

(56) References Cited

U.S. PATENT DOCUMENTS

| | | | |
|---|---|---|---|
| 5,911,222 A * | | 6/1999 | Lawrence ............... A61F 5/455 600/573 |
| 5,957,904 A | | 9/1999 | Holland |
| 5,972,505 A | | 10/1999 | Phillips et al. |
| 6,059,762 A | | 5/2000 | Boyer et al. |
| 6,063,064 A | | 5/2000 | Tuckey et al. |
| 6,098,625 A | | 8/2000 | Winkler |
| 6,105,174 A | | 8/2000 | Karlsten et al. |
| 6,113,582 A | | 9/2000 | Dwork |
| 6,117,163 A * | | 9/2000 | Bierman ............... A61M 25/02 606/232 |
| 6,123,398 A * | | 9/2000 | Arai .................... B60T 8/17552 303/151 |
| 6,129,718 A | | 10/2000 | Wada et al. |
| 6,131,964 A | | 10/2000 | Sareshwala |
| 6,152,902 A | | 11/2000 | Christian et al. |
| 6,164,569 A | | 12/2000 | Hollinshead et al. |
| 6,177,606 B1 | | 1/2001 | Etheredge et al. |
| 6,209,142 B1 | | 4/2001 | Mattsson et al. |
| 6,248,096 B1 | | 6/2001 | Dwork et al. |
| 6,263,887 B1 | | 7/2001 | Dunn |
| 6,311,339 B1 | | 11/2001 | Kraus |
| 6,336,919 B1 | | 1/2002 | Davis et al. |
| 6,338,729 B1 | | 1/2002 | Wada et al. |
| 6,352,525 B1 | | 3/2002 | Wakabayashi |
| 6,409,712 B1 | | 6/2002 | Dutari et al. |
| 6,416,500 B1 | | 7/2002 | Wada et al. |
| 6,428,521 B1 | | 8/2002 | Droll |
| 6,475,198 B1 | | 11/2002 | Lipman et al. |
| 6,479,726 B1 | | 11/2002 | Cole et al. |
| 6,491,673 B1 | | 12/2002 | Palumbo et al. |
| 6,508,794 B1 | | 1/2003 | Palumbo et al. |
| 6,540,729 B1 | | 4/2003 | Wada et al. |
| 6,547,771 B2 | | 4/2003 | Robertson et al. |
| 6,569,133 B2 | | 5/2003 | Cheng et al. |
| D476,518 S | | 7/2003 | Doppelt |
| 6,592,560 B2 | | 7/2003 | Snyder et al. |
| 6,618,868 B2 | | 9/2003 | Minnick |
| 6,620,142 B1 | | 9/2003 | Flueckiger |
| 6,629,651 B1 | | 10/2003 | Male et al. |
| 6,635,038 B2 | | 10/2003 | Scovel |
| 6,652,495 B1 | | 11/2003 | Walker |
| 6,685,684 B1 | | 2/2004 | Falconer |
| 6,702,793 B1 | | 3/2004 | Sweetser et al. |
| 6,706,027 B2 * | | 3/2004 | Harvie ................... A61F 5/453 604/326 |
| 6,732,384 B2 * | | 5/2004 | Scott ..................... A47K 11/12 4/144.1 |
| 6,740,066 B2 * | | 5/2004 | Wolff .................... A61F 5/451 604/323 |
| 6,764,477 B1 | | 7/2004 | Chen et al. |
| 6,783,519 B2 | | 8/2004 | Samuelsson |
| 6,796,974 B2 | | 9/2004 | Palumbo et al. |
| 6,814,547 B2 | | 11/2004 | Childers et al. |
| 6,849,065 B2 | | 2/2005 | Schmidt et al. |
| 6,857,137 B2 | | 2/2005 | Otto |
| 6,885,690 B2 | | 4/2005 | Aggerstam et al. |
| 6,888,044 B2 | | 5/2005 | Fell et al. |
| 6,893,425 B2 | | 5/2005 | Dunn et al. |
| 6,912,737 B2 | | 7/2005 | Ernest et al. |
| 6,918,899 B2 * | | 7/2005 | Harvie ................... A61F 5/451 604/326 |
| 6,979,324 B2 | | 12/2005 | Bybordi et al. |
| 7,018,366 B2 * | | 3/2006 | Easter ................... A61F 5/451 604/327 |
| 7,066,411 B2 | | 6/2006 | Male et al. |
| 7,125,399 B2 | | 10/2006 | Miskie |
| 7,131,964 B2 * | | 11/2006 | Harvie ................... A61F 5/455 604/326 |
| 7,135,012 B2 * | | 11/2006 | Harvie ................... A61F 5/453 604/326 |
| 7,141,043 B2 * | | 11/2006 | Harvie ................... A61F 5/451 604/326 |
| D533,972 S | | 12/2006 | La |
| 7,160,273 B2 | | 1/2007 | Greter et al. |
| 7,171,699 B2 | | 2/2007 | Ernest et al. |
| 7,171,871 B2 | | 2/2007 | Kozak |
| 7,179,951 B2 | | 2/2007 | Krishnaswamy-mirle et al. |
| 7,181,781 B1 | | 2/2007 | Trabold et al. |
| 7,186,245 B1 | | 3/2007 | Cheng et al. |
| 7,192,424 B2 | | 3/2007 | Cooper |
| 7,220,250 B2 * | | 5/2007 | Suzuki ................... A61F 5/451 604/328 |
| D562,975 S | | 2/2008 | Otto |
| 7,335,189 B2 * | | 2/2008 | Harvie ................... A61F 5/451 604/326 |
| 7,358,282 B2 | | 4/2008 | Krueger et al. |
| 7,390,320 B2 * | | 6/2008 | Machida ................. A61F 5/455 4/144.1 |
| 7,438,706 B2 | | 10/2008 | Koizumi et al. |
| 7,488,310 B2 | | 2/2009 | Yang |
| D591,106 S | | 4/2009 | Dominique et al. |
| 7,513,381 B2 | | 4/2009 | Heng et al. |
| 7,520,872 B2 | | 4/2009 | Biggie et al. |
| D593,801 S | | 6/2009 | Wilson et al. |
| 7,540,364 B2 | | 6/2009 | Sanderson |
| 7,588,560 B1 | | 9/2009 | Dunlop |
| 7,665,359 B2 | | 2/2010 | Barber |
| 7,682,347 B2 | | 3/2010 | Parks et al. |
| 7,687,004 B2 | | 3/2010 | Allen |
| 7,695,459 B2 | | 4/2010 | Gilbert et al. |
| 7,695,460 B2 | | 4/2010 | Wada et al. |
| 7,699,818 B2 | | 4/2010 | Gilbert |
| 7,699,831 B2 * | | 4/2010 | Bengtson ................. A61M 1/90 604/313 |
| 7,722,584 B2 | | 5/2010 | Tanaka et al. |
| 7,727,206 B2 | | 6/2010 | Gorres |
| 7,740,620 B2 | | 6/2010 | Gilbert et al. |
| 7,749,205 B2 * | | 7/2010 | Tazoe .................... A61F 5/451 604/320 |
| 7,755,497 B2 * | | 7/2010 | Wada ..................... A61F 5/451 340/604 |
| 7,766,887 B2 | | 8/2010 | Burns, Jr. et al. |
| D625,407 S | | 10/2010 | Koizumi et al. |
| 7,806,879 B2 | | 10/2010 | Brooks et al. |
| 7,815,067 B2 | | 10/2010 | Matsumoto et al. |
| 7,833,169 B2 | | 11/2010 | Hannon |
| 7,857,806 B2 | | 12/2010 | Karpowicz et al. |
| 7,866,942 B2 | | 1/2011 | Harvie |
| 7,871,385 B2 | | 1/2011 | Levinson et al. |
| 7,875,010 B2 | | 1/2011 | Frazier et al. |
| 7,901,389 B2 | | 3/2011 | Mombrinie |
| 7,927,320 B2 | | 4/2011 | Goldwasser et al. |
| 7,927,321 B2 | | 4/2011 | Marland |
| 7,931,634 B2 | | 4/2011 | Swiecicki et al. |
| 7,939,706 B2 * | | 5/2011 | Okabe .................... A61F 5/4404 604/361 |
| 7,946,443 B2 | | 5/2011 | Stull et al. |
| 7,947,025 B2 | | 5/2011 | Buglino et al. |
| 7,963,419 B2 | | 6/2011 | Burney et al. |
| 7,976,519 B2 | | 7/2011 | Bubb et al. |
| 7,993,318 B2 | | 8/2011 | Olsson et al. |
| 8,028,460 B2 | | 10/2011 | Williams |
| 8,047,398 B2 | | 11/2011 | Dimartino et al. |
| 8,083,094 B2 | | 12/2011 | Caulfield et al. |
| 8,128,608 B2 * | | 3/2012 | Thevenin ................ A61F 13/84 604/347 |
| 8,181,651 B2 | | 5/2012 | Pinel |
| 8,181,819 B2 | | 5/2012 | Burney et al. |
| 8,211,063 B2 * | | 7/2012 | Bierman ................. A61M 25/02 604/179 |
| 8,221,369 B2 | | 7/2012 | Parks et al. |
| 8,241,262 B2 | | 8/2012 | Mahnensmith |
| 8,277,426 B2 | | 10/2012 | Wilcox et al. |
| 8,287,508 B1 * | | 10/2012 | Sanchez ................. A61F 5/4404 604/326 |
| 8,303,554 B2 | | 11/2012 | Tsai et al. |
| 8,322,565 B2 | | 12/2012 | Caulfield et al. |
| 8,337,477 B2 | | 12/2012 | Parks et al. |
| D674,241 S | | 1/2013 | Bickert et al. |
| 8,343,122 B2 | | 1/2013 | Gorres |
| 8,353,074 B2 | | 1/2013 | Krebs |

(56) References Cited

U.S. PATENT DOCUMENTS

| | | | |
|---|---|---|---|
| 8,353,886 B2 | 1/2013 | Bester et al. | |
| D676,241 S | 2/2013 | Merrill | |
| 8,388,588 B2 | 3/2013 | Wada et al. | |
| D679,807 S | 4/2013 | Burgess et al. | |
| 8,425,482 B2 | 4/2013 | Khoubnazar | |
| 8,449,510 B2 | 5/2013 | Martini et al. | |
| D684,260 S | 6/2013 | Lund et al. | |
| 8,470,230 B2 | 6/2013 | Caulfield et al. | |
| 8,479,941 B2 | 7/2013 | Matsumoto et al. | |
| 8,479,949 B2 | 7/2013 | Henkel | |
| 8,529,530 B2 | 9/2013 | Koch et al. | |
| 8,535,284 B2 | 9/2013 | Joder et al. | |
| 8,546,639 B2 * | 10/2013 | Wada | A61F 5/4401 604/361 |
| 8,551,075 B2 * | 10/2013 | Bengtson | A61M 1/84 604/543 |
| 8,568,376 B2 | 10/2013 | Delattre et al. | |
| D694,404 S | 11/2013 | Burgess et al. | |
| 8,585,683 B2 * | 11/2013 | Bengtson | A61M 27/00 604/543 |
| 8,652,112 B2 | 2/2014 | Johannison et al. | |
| D702,973 S | 4/2014 | Norland et al. | |
| 8,703,032 B2 | 4/2014 | Menon et al. | |
| D704,330 S | 5/2014 | Cicatelli | |
| D704,510 S | 5/2014 | Mason et al. | |
| D705,423 S | 5/2014 | Walsh Cutler | |
| D705,926 S | 5/2014 | Burgess et al. | |
| 8,714,394 B2 | 5/2014 | Wulf | |
| 8,715,267 B2 | 5/2014 | Bengtson et al. | |
| 8,757,425 B2 | 6/2014 | Copeland | |
| 8,777,032 B2 | 7/2014 | Biesecker et al. | |
| 8,808,260 B2 | 8/2014 | Koch et al. | |
| 8,864,730 B2 | 10/2014 | Conway et al. | |
| 8,881,923 B2 | 11/2014 | Higginson | |
| 8,936,585 B2 | 1/2015 | Carson et al. | |
| D729,581 S | 5/2015 | Boroski | |
| 9,028,460 B2 * | 5/2015 | Medeiros | A61F 5/451 604/347 |
| 9,056,698 B2 | 6/2015 | Noer | |
| 9,078,792 B2 | 7/2015 | Ruiz | |
| 9,173,602 B2 | 11/2015 | Gilbert | |
| 9,173,799 B2 * | 11/2015 | Tanimoto | A61F 5/453 |
| 9,187,220 B2 | 11/2015 | Biesecker et al. | |
| 9,199,772 B2 | 12/2015 | Krippendorf | |
| 9,248,058 B2 | 2/2016 | Conway et al. | |
| 9,308,118 B1 | 4/2016 | Dupree et al. | |
| 9,309,029 B2 | 4/2016 | Incorvia et al. | |
| 9,333,281 B2 | 5/2016 | Giezendanner et al. | |
| 9,382,047 B2 | 7/2016 | Schmidtner et al. | |
| 9,456,937 B2 | 10/2016 | Ellis | |
| 9,480,595 B2 | 11/2016 | Baham et al. | |
| 9,517,865 B2 | 12/2016 | Albers et al. | |
| D777,941 S | 1/2017 | Piramoon | |
| 9,533,806 B2 | 1/2017 | Ding et al. | |
| 9,550,611 B2 | 1/2017 | Hodge | |
| 9,555,930 B2 | 1/2017 | Campbell et al. | |
| D789,522 S | 6/2017 | Burgess et al. | |
| 9,687,849 B2 | 6/2017 | Bruno et al. | |
| 9,694,949 B2 | 7/2017 | Hendricks et al. | |
| 9,788,992 B2 | 10/2017 | Harvie | |
| D804,907 S | 12/2017 | Sandoval | |
| 9,868,564 B2 | 1/2018 | McGirr et al. | |
| D814,239 S | 4/2018 | Arora | |
| D817,484 S | 5/2018 | Lafond | |
| 10,037,640 B2 | 7/2018 | Gordon | |
| 10,058,470 B2 | 8/2018 | Phillips | |
| 10,098,990 B2 | 10/2018 | Koch et al. | |
| D835,264 S | 12/2018 | Mozzicato et al. | |
| D835,779 S | 12/2018 | Mozzicato et al. | |
| D840,533 S | 2/2019 | Mozzicato et al. | |
| D840,534 S | 2/2019 | Mozzicato et al. | |
| 10,225,376 B2 | 3/2019 | Perez Martinez | |
| 10,226,376 B2 * | 3/2019 | Sanchez | A61F 5/455 |
| D848,612 S | 5/2019 | Mozzicato et al. | |
| 10,307,305 B1 | 6/2019 | Hodges | |
| 10,335,121 B2 | 7/2019 | Desai | |
| D856,512 S | 8/2019 | Cowart et al. | |
| 10,376,406 B2 | 8/2019 | Newton | |
| 10,376,407 B2 | 8/2019 | Newton | |
| 10,390,989 B2 * | 8/2019 | Sanchez | A61F 5/453 |
| D858,144 S | 9/2019 | Fu | |
| 10,406,039 B2 | 9/2019 | Villarreal | |
| 10,407,222 B2 | 9/2019 | Allen | |
| 10,478,356 B2 | 11/2019 | Griffin | |
| 10,538,366 B2 | 1/2020 | Pentelovitch et al. | |
| 10,569,938 B2 | 2/2020 | Zhao et al. | |
| 10,577,156 B2 | 3/2020 | Dagnelie et al. | |
| 10,618,721 B2 | 4/2020 | Vazin | |
| D884,390 S | 5/2020 | Wang | |
| 10,669,079 B2 | 6/2020 | Freedman et al. | |
| D892,315 S | 8/2020 | Airy | |
| 10,730,672 B2 | 8/2020 | Bertram et al. | |
| 10,737,848 B2 | 8/2020 | Philip et al. | |
| 10,765,854 B2 | 9/2020 | Law et al. | |
| 10,766,670 B2 | 9/2020 | Kittmann | |
| D901,214 S | 11/2020 | Hu | |
| 10,865,017 B1 | 12/2020 | Cowart et al. | |
| 10,889,412 B2 | 1/2021 | West et al. | |
| 10,913,581 B2 | 2/2021 | Stahlecker | |
| D912,244 S | 3/2021 | Rehm et al. | |
| 10,952,889 B2 * | 3/2021 | Newton | A61F 5/4404 |
| 10,973,678 B2 | 4/2021 | Newton et al. | |
| 10,974,874 B2 | 4/2021 | Ragias et al. | |
| 11,000,401 B2 | 5/2021 | Ecklund et al. | |
| D923,365 S | 6/2021 | Wang | |
| 11,027,900 B2 | 6/2021 | Liu | |
| 11,045,346 B2 | 6/2021 | Argent et al. | |
| D928,946 S * | 8/2021 | Sanchez | D24/122 |
| 11,179,506 B2 | 11/2021 | Barr et al. | |
| 11,226,376 B2 | 1/2022 | Yamauchi et al. | |
| 2001/0037097 A1 | 11/2001 | Cheng et al. | |
| 2001/0054426 A1 | 12/2001 | Knudson et al. | |
| 2002/0019614 A1 * | 2/2002 | Woon | A61F 13/53747 604/378 |
| 2002/0026161 A1 | 2/2002 | Grundke | |
| 2002/0087131 A1 * | 7/2002 | Wolff | A61B 5/20 604/327 |
| 2002/0189992 A1 | 12/2002 | Schmidt et al. | |
| 2003/0004436 A1 | 1/2003 | Schmidt et al. | |
| 2003/0120178 A1 | 6/2003 | Heki | |
| 2003/0157859 A1 | 8/2003 | Ishikawa | |
| 2003/0181880 A1 | 9/2003 | Schwartz | |
| 2003/0195484 A1 * | 10/2003 | Harvie | A61F 5/455 604/355 |
| 2003/0233079 A1 | 12/2003 | Parks et al. | |
| 2004/0006321 A1 | 1/2004 | Cheng et al. | |
| 2004/0056122 A1 | 3/2004 | Male et al. | |
| 2004/0084465 A1 | 5/2004 | Luburic | |
| 2004/0127872 A1 * | 7/2004 | Petryk | A61F 13/49 604/382 |
| 2004/0128749 A1 | 7/2004 | Scott | |
| 2004/0143229 A1 * | 7/2004 | Easter | A61F 5/451 604/322 |
| 2004/0176731 A1 | 9/2004 | Cheng et al. | |
| 2004/0191919 A1 | 9/2004 | Unger et al. | |
| 2004/0207530 A1 * | 10/2004 | Nielsen | A61F 13/42 340/573.5 |
| 2004/0236292 A1 * | 11/2004 | Tazoe | A61F 5/451 604/317 |
| 2004/0254547 A1 * | 12/2004 | Okabe | A61F 5/455 604/317 |
| 2005/0010182 A1 | 1/2005 | Parks et al. | |
| 2005/0033248 A1 * | 2/2005 | Machida | A61F 5/455 604/327 |
| 2005/0070861 A1 * | 3/2005 | Okabe | A61F 5/4404 604/327 |
| 2005/0070862 A1 * | 3/2005 | Tazoe | A61F 5/441 604/327 |
| 2005/0082300 A1 | 4/2005 | Modrell et al. | |
| 2005/0097662 A1 | 5/2005 | Leimkuhler et al. | |
| 2005/0101924 A1 | 5/2005 | Elson et al. | |
| 2005/0137557 A1 | 6/2005 | Swiecicki et al. | |
| 2005/0177070 A1 | 8/2005 | Levinson et al. | |

(56) References Cited

U.S. PATENT DOCUMENTS

| | | |
|---|---|---|
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1* | 1/2006 | Suzuki ............... A61F 5/451 604/329 |
| 2006/0016778 A1 | 1/2006 | Park |
| 2006/0111648 A1 | 5/2006 | Vermaak |
| 2006/0155214 A1* | 7/2006 | Wightman ............ A61F 5/455 600/574 |
| 2006/0200102 A1 | 9/2006 | Cooper |
| 2006/0229576 A1 | 10/2006 | Conway et al. |
| 2006/0231648 A1 | 10/2006 | Male et al. |
| 2006/0235359 A1 | 10/2006 | Marland |
| 2007/0006368 A1 | 1/2007 | Key et al. |
| 2007/0038194 A1* | 2/2007 | Wada ................... A61F 5/451 604/347 |
| 2007/0117880 A1 | 5/2007 | Elson et al. |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0225666 A1 | 9/2007 | Otto |
| 2007/0225668 A1 | 9/2007 | Otto |
| 2007/0266486 A1 | 11/2007 | Ramirez |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1* | 2/2008 | Okabe .................. A61F 5/4404 604/378 |
| 2008/0041869 A1 | 2/2008 | Backaert |
| 2008/0091153 A1* | 4/2008 | Harvie ................. A61F 5/451 604/318 |
| 2008/0091158 A1 | 4/2008 | Yang |
| 2008/0234642 A1 | 9/2008 | Patterson et al. |
| 2008/0281282 A1 | 11/2008 | Finger et al. |
| 2008/0287894 A1* | 11/2008 | Van Den Heuvel .... A61F 5/455 604/327 |
| 2009/0025717 A1 | 1/2009 | Pinel |
| 2009/0056003 A1 | 3/2009 | Ivie et al. |
| 2009/0192482 A1* | 7/2009 | Dodge, II .............. A61L 15/60 524/436 |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1* | 10/2009 | Medeiros .............. A61F 5/451 604/347 |
| 2009/0281510 A1 | 11/2009 | Fisher |
| 2010/0004612 A1* | 1/2010 | Thevenin .............. A61F 13/84 4/443 |
| 2010/0058660 A1 | 3/2010 | Williams |
| 2010/0121289 A1 | 5/2010 | Parks et al. |
| 2010/0185168 A1* | 7/2010 | Graauw ................ A61F 5/4556 604/347 |
| 2010/0198172 A1 | 8/2010 | Wada et al. |
| 2010/0211032 A1* | 8/2010 | Tsai ..................... A61F 5/453 604/319 |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1* | 2/2011 | Wada ................... A61F 5/4401 604/318 |
| 2011/0040271 A1 | 2/2011 | Rogers et al. |
| 2011/0054426 A1 | 3/2011 | Stewart et al. |
| 2011/0060300 A1* | 3/2011 | Weig .................... A61M 1/0003 604/319 |
| 2011/0077495 A1 | 3/2011 | Gilbert |
| 2011/0137273 A1 | 6/2011 | Muellejans et al. |
| 2011/0172620 A1 | 7/2011 | Khambatta |
| 2011/0172625 A1* | 7/2011 | Wada .................... A61F 13/42 604/385.01 |
| 2011/0202024 A1 | 8/2011 | Cozzens |
| 2011/0240648 A1 | 10/2011 | Tucker |
| 2011/0265889 A1 | 11/2011 | Tanaka et al. |
| 2012/0035577 A1 | 2/2012 | Tomes et al. |
| 2012/0066825 A1 | 3/2012 | Birbara et al. |
| 2012/0103347 A1* | 5/2012 | Wheaton .............. A61F 5/453 128/885 |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245542 A1* | 9/2012 | Suzuki ................. A61F 13/84 374/45 |
| 2012/0245547 A1 | 9/2012 | Wilcox et al. |
| 2012/0253303 A1* | 10/2012 | Suzuki ................. A61F 13/42 374/45 |
| 2012/0330256 A1 | 12/2012 | Wilcox et al. |
| 2013/0006206 A1* | 1/2013 | Wada .................... A61F 13/535 604/385.01 |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0245496 A1 | 9/2013 | Wells et al. |
| 2013/0292537 A1 | 11/2013 | Dirico |
| 2014/0031774 A1* | 1/2014 | Bengtson .............. A61M 1/84 604/319 |
| 2014/0157499 A1 | 6/2014 | Suzuki et al. |
| 2014/0182051 A1* | 7/2014 | Tanimoto .............. A61G 9/006 4/144.3 |
| 2014/0196189 A1 | 7/2014 | Lee et al. |
| 2014/0276501 A1 | 9/2014 | Cisko |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290475 A1 | 10/2015 | Macy et al. |
| 2015/0320583 A1 | 11/2015 | Harvie |
| 2015/0329255 A1 | 11/2015 | Rzepecki |
| 2015/0359660 A1* | 12/2015 | Harvie ................. A61F 5/441 604/351 |
| 2015/0366699 A1 | 12/2015 | Nelson |
| 2016/0029998 A1 | 2/2016 | Brister et al. |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1* | 4/2016 | Timm .................. A61F 13/84 604/385.01 |
| 2016/0278662 A1 | 9/2016 | Brister et al. |
| 2016/0366699 A1 | 12/2016 | Zhang et al. |
| 2016/0367226 A1* | 12/2016 | Newton ............... A01K 23/005 |
| 2016/0367411 A1 | 12/2016 | Justiz et al. |
| 2016/0374848 A1* | 12/2016 | Sanchez ............... A61F 5/453 604/319 |
| 2017/0007438 A1* | 1/2017 | Harvie ................. A61F 5/453 |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ............... A61F 5/4404 |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |

(56) References Cited

U.S. PATENT DOCUMENTS

| | | |
|---|---|---|
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1* | 12/2017 | Newton ............... A61F 5/4404 |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0028349 A1* | 2/2018 | Newton ............... A61F 5/453 |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0127187 A1 | 5/2018 | Sewell |
| 2018/0200101 A1 | 7/2018 | Su |
| 2018/0228642 A1* | 8/2018 | Davis ............... A61F 5/451 |
| 2019/0021899 A1 | 1/2019 | Vlet |
| 2019/0038451 A1* | 2/2019 | Harvie ............... A61F 5/441 |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1* | 5/2019 | Sanchez ............... A61F 5/4404 |
| | | 604/319 |
| 2019/0224036 A1* | 7/2019 | Sanchez ............... A61F 5/443 |
| 2019/0247222 A1 | 8/2019 | Ecklund et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0046544 A1* | 2/2020 | Godinez ............... A61F 5/451 |
| 2020/0055638 A1 | 2/2020 | Lau et al. |
| 2020/0070392 A1 | 3/2020 | Huber et al. |
| 2020/0085610 A1 | 3/2020 | Cohn et al. |
| 2020/0171217 A9 | 6/2020 | Braga et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0255189 A1 | 8/2020 | Liu |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0385179 A1 | 12/2020 | McCourt |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0061523 A1 | 3/2021 | Bytheway |
| 2021/0069005 A1* | 3/2021 | Sanchez ............... A61F 5/4405 |
| 2021/0069008 A1 | 3/2021 | Blabas et al. |
| 2021/0121318 A1 | 4/2021 | Pinlac |
| 2021/0137724 A1 | 5/2021 | Ecklund et al. |
| 2021/0154055 A1 | 5/2021 | Villarreal |
| 2021/0170079 A1 | 6/2021 | Radl et al. |
| 2021/0220162 A1 | 7/2021 | Jamison |
| 2021/0220163 A1 | 7/2021 | Mayrand |
| 2021/0229877 A1 | 7/2021 | Ragias et al. |
| 2021/0267787 A1 | 9/2021 | Nazemi |
| 2021/0386925 A1 | 12/2021 | Hartwell et al. |
| 2022/0023091 A1 | 1/2022 | Ecklund et al. |
| 2022/0066825 A1 | 3/2022 | Saraf et al. |

FOREIGN PATENT DOCUMENTS

| | | |
|---|---|---|
| CA | 3098571 A1 | 11/2019 |
| CN | 2269203 Y | 12/1997 |
| CN | 1332620 A | 1/2002 |
| CN | 1533755 A | 10/2004 |
| CN | 1602825 A | 4/2005 |
| CN | 1720888 A | 1/2006 |
| CN | 101262836 A | 9/2008 |
| CN | 202184840 U | 4/2012 |
| CN | 103717180 A | 4/2014 |
| CN | 205849719 U | 1/2017 |
| CN | 107847384 A | 3/2018 |
| CN | 107920912 A | 4/2018 |
| CN | 209285902 U | 8/2019 |
| DE | 79818 C | 10/1893 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 19619597 A1 | 11/1997 |
| DE | 102011103783 A1 | 12/2012 |
| DE | 202015104597 U1 | 7/2016 |
| DK | 9600118 | 11/1996 |
| EP | 0032138 A2 | 7/1981 |
| EP | 0066070 B1 | 12/1982 |
| EP | 0119143 B1 | 11/1988 |
| EP | 0610638 A1 | 8/1994 |
| EP | 0613355 A1 | 9/1994 |
| EP | 0613355 B1 | 1/1997 |
| EP | 1332738 A1 | 8/2003 |
| EP | 1382318 A1 | 1/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2676643 A1 | 12/2013 |
| EP | 2997950 A2 | 3/2016 |
| EP | 2879534 B1 | 3/2017 |
| EP | 3169292 B1 | 11/2019 |
| EP | 3752110 B1 | 3/2022 |
| GB | 1011517 A | 12/1965 |
| GB | 1467144 A | 3/1977 |
| GB | 2106395 A | 4/1983 |
| GB | 2171315 A | 8/1986 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| IT | 201800009129 A1 | 4/2020 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H0460220 A | 2/1992 |
| JP | H05123349 A | 5/1993 |
| JP | 3087938 B2 | 10/1995 |
| JP | H1040141 A | 2/1998 |
| JP | H11113946 A | 4/1999 |
| JP | H11290365 A | 10/1999 |
| JP | 2000185068 A | 7/2000 |
| JP | 3087938 B2 | 9/2000 |
| JP | 2001054531 A | 2/2001 |
| JP | 2001070331 A | 3/2001 |
| JP | 2001276107 A | 10/2001 |
| JP | 2001276108 A | 10/2001 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 2006026108 A | 2/2006 |
| JP | 3123547 B2 | 6/2006 |
| JP | 2006204868 A | 8/2006 |
| JP | 3132659 B2 | 5/2007 |
| JP | 4039641 B2 | 11/2007 |
| JP | 2010081981 A | 4/2010 |

(56) References Cited

FOREIGN PATENT DOCUMENTS

| | | |
|---|---|---|
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011224070 A | 11/2011 |
| JP | 2012523869 A | 10/2012 |
| JP | 2015092945 A | 5/2015 |
| JP | 3198994 B2 | 7/2015 |
| JP | 2019525811 A | 9/2019 |
| KR | 20030047451 A | 6/2003 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0033773 A1 | 6/2000 |
| WO | 0057784 A1 | 10/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005074571 A3 | 9/2005 |
| WO | 2005089687 A2 | 9/2005 |
| WO | 2005107661 A2 | 11/2005 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001846 A1 | 1/2017 |
| WO | 2017152198 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018150267 A3 | 11/2018 |
| WO | 2018235065 A1 | 12/2018 |
| WO | 2019004404 A1 | 1/2019 |
| WO | 2019065541 A1 | 4/2019 |
| WO | 2019188566 A1 | 10/2019 |
| WO | 2019214787 A1 | 11/2019 |
| WO | WO-2019212949 A1 * | 11/2019 ............. A61F 5/451 |
| WO | WO-2019212951 A1 * | 11/2019 ............. A61F 5/455 |
| WO | WO-2019212954 A1 * | 11/2019 ............. A61F 5/451 |
| WO | 2020038822 A1 | 2/2020 |
| WO | 2020120657 A1 | 6/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021016026 A1 | 1/2021 |
| WO | 2021034886 A1 | 2/2021 |
| WO | 2021094352 A1 | 5/2021 |
| WO | 2021155206 A1 | 8/2021 |
| WO | 2021173436 A1 | 9/2021 |
| WO | 2021207621 A1 | 10/2021 |
| WO | 2021257202 A1 | 12/2021 |
| WO | 2022006256 A1 | 1/2022 |

OTHER PUBLICATIONS

Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.

(56) References Cited

OTHER PUBLICATIONS

AMXDmax In-Flight Bladder Relief; Omni Medical 2015; Omni Medical Systems, Inc.
Corrected International Search Report and Written Opinion for International Application No. PCT/US2017/043025 dated Jan. 11, 2018.
Corrected Notice of Allowability for U.S. Appl. No. 15/221,106 dated Jul. 2, 2019.
Final Office Action for U.S. Appl. No. 14/722,613 dated Nov. 29, 2018.
Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 15/171,968 dated Feb. 14, 2020.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 29/624,661 dated Feb. 18, 2020.
International Search Report and Written Opinion from International Application No. PCT/US2016/049274 dated Dec. 1, 2016.
International Search Report and Written Opinion from International Application No. PCT/US2017/035625 dated Aug. 15, 2017.
International Search Report and Written Opinion from International Application No. PCT/US2017/043025 dated Oct. 18, 2017.
International Search Report and Written Opinion from International Application No. PCT/US2018/015968 dated Apr. 6, 2018.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Issue Notification for U.S. Appl. No. 15/611,587 dated Feb. 20, 2019.
Non-Final Office Action for U.S. Appl. No. 14/722,613 dated Jun. 13, 2019.
Non-Final Office Action for U.S. Appl. No. 14/947,759, dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Jun. 12, 2018.
Non-Final Office Action for U.S. Appl. No. 15/171,968 dated Aug. 20, 2019.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 29/624,661 dated Jul. 18, 2019.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 29/624,661 dated May 14, 2020.
U.S. Appl. No. 15/171,968, filed Jun. 2, 2016.
U.S. Appl. No. 15/221,106, filed Jul. 27, 2016.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
Defendant and Counterclaim Plaintiff Sage Products, LLC's Answer, Defenses, and Counterclaims to Plaintiff's Amended Complaint, Nov. 1, 2019.
"Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
"Step by Step How Ur24 WorksHome", http://medicalpatentur24.com, last accessed Dec. 6, 2017, Aug. 30, 2017, 4 pages.
Parmar, "10 Finalists Chosen for Dare-to-Dream Medtech Design Challenge (PureWick)," Design Services, Nov. 10, 2014 (3 pages).
Purewick, "Incontinence Relief for Women" Presentation, (7 pages), Sep. 23, 2015.
Pytlik, "Super Absorbent Polymers," University of Buffalo http://www.courses.sens.buffalo.edu/ce435/Diapers/Diapers.html, accessed on Feb. 17, 2017.
Non-Final Office Action for U.S. Appl. No. 29/694,002 dated Jun. 24, 2020.

(56) References Cited

OTHER PUBLICATIONS

Notice of Allowance for U.S. Appl. No. 29/624,661 dated Jul. 10, 2020.
U.S. Appl. No. 16/904,868, filed Jun. 18, 2020.
PureWick's Response to Interrogatory No. 9 in *PureWick, LLC* v. *Sage Products, LLC*, Case No. 19-1508-MN, 2020, 6 pages.
"Underwear that absorbs your period", Thinx!, https://www.shethinx.com/pages/thinx-it-works last accessed Jun. 24, 2020, 7 pages.
Hollister, "Retracted Penis Pouch by Hollister", Vitality Medical.com, https://www.vitalitymedical.com/hollister-retracted-penis-pouch.html last accessed Jun. 24, 2020, 6 pages.
Newman, "Declaration of Diane K. Newman Curriculum Vitae", Petition for Interparties Review, 2020, pp. 1-199.
Newman, et al., "The Urinary Incontinence Sourcebook", Petition for Interparties Review, 1997, 23 pages.
Advisory Action for U.S. Appl. No. 16/904,868 dated Jul. 2, 2021.
Advisory Action for U.S. Appl. No. 16/905,400 dated Jun. 9, 2021.
Corrected Notice of Allowability for U.S. Appl. No. 15/612,325 dated Mar. 17, 2021.
Final Office Action for U.S. Appl. No. 14/952,591 dated Nov. 27, 2020.
Final Office Action for U.S. Appl. No. 15/612,325 dated Sep. 17, 2020.
Final Office Action for U.S. Appl. No. 16/899,956 dated Apr. 19, 2021.
Final Office Action for U.S. Appl. No. 16/904,868 dated Mar. 26, 2021.
Final Office Action for U.S. Appl. No. 17/088,272 dated May 25, 2021.
International Search Report and Written Opinion from International Application No. PCT/US2021/023001 dated Jun. 21, 2021.
Issue Notification for U.S. Appl. No. 15/171,968 dated Mar. 3, 2021.
Issue Notification for U.S. Appl. No. 15/612,325 dated Mar. 24, 2021.
Non-Final Office Action for U.S. Appl. No. 16/899,956 dated Oct. 16, 2020.
Non-Final Office Action for U.S. Appl. No. 16/904,868 dated Nov. 25, 2020.
Non-Final Office Action for U.S. Appl. No. 17/088,272 dated Jan. 25, 2021.
Notice of Allowance for U.S. Appl. No. 14/952,591 dated Apr. 5, 2021.
Notice of Allowance for U.S. Appl. No. 15/171,968 dated Feb. 16, 2021.
Notice of Allowance for U.S. Appl. No. 15/171,968 dated Nov. 6, 2020.
Notice of Allowance for U.S. Appl. No. 15/612,325 dated Feb. 19, 2021.
Notice of Allowance for U.S. Appl. No. 15/612,325 dated Jan. 21, 2021.
Notice of Allowance for U.S. Appl. No. 29/624,661 dated Apr. 28, 2021.
Notice of Allowance for U.S. Appl. No. 29/624,661 dated Sep. 29, 2020.
Notice of Allowance for U.S. Appl. No. 29/694,002 dated Apr. 29, 2021.
Notice of Allowance for U.S. Appl. No. 29/694,002 dated Jan. 29, 2021.
Notice of Allowance for U.S. Appl. No. 29/694,002 dated Oct. 16, 2020.
Notice to File Missing Parts for U.S. Appl. No. 17/179,116 dated Mar. 3, 2021.
Restriction Requirement for U.S. Appl. No. 16/478,180 dated May 25, 2021.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657 mailed May 26, 2021.
Memorandum Order, Feb. 2021, 14 pgs.
Sage's Initial Invalidity Contentions Regarding U.S. Pat. Nos. 8,287,508 10,226,375; and 10,390,989, May 29, 2020, 193 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. Nos. 8,287,508, 10,226,375, 10,390,989, and 10,376,407, 292 pages.
Boehringer CareDry System—Second Generation for Non-lnvasive Urinary Management for Females, Mar. 2021, 3 pgs.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
Sage's Preliminary Identification of Claim Elements and Proposed Constructions for U.S. Pat. Nos. 8,287,508, 10,226,376, 10,390,989 and 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, U.S. Pat. No. 8,287,508, 2020, 2 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDX—Advanced Mission Extender Device Brochure", Omni Medical, Omni Brochure—http://www.omnimedicalsys.com/uploads/AMXDFixedWing.pdf, 2 pages.
"How Period Panties Work", www.shethinx.com/pages/thinx-itworks, 2020, 10 pages.
"In Flight Bladder Relief", Omni Medical, Omni Presentation https://www.omnimedicalsys.com/uploads/AMXDmax_HSD.pdf, 14 pages.
"Research and Development Work Relating to Assistive Technology Jun. 2005", British Department of Health, Nov. 2006, 40 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
MacAulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newton, et al., "Measuring Safety, Effectiveness and Ease of Use of PureWick in the Management of Urinary Incontinence in Bedbound Women: Case Studies", Jan. 8, 2016, 11 pages.
Sachtman, "New Relief for Pilots? It Depends", Wired, https://www.wired.com/2008/05/pilot-relief/, 2008, 2 pages.
Advisory Action for U.S. Appl. No. 16/899,956 dated Jul. 9, 2021.
International Search Report and Written Opinion from International Application No. PCT/US2020/023572 dated Jul. 6, 2020.
International Search Report and Written Opinion from International Application No. PCT/US2020/033064 dated Aug. 31, 2020.
International Search Report and Written Opinion from International Application No. PCT/US2020/033122 dated Aug. 31, 2020.
International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.

(56) References Cited

OTHER PUBLICATIONS

International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015024 dated May 18, 2021.
International Search Report and Written Opinion from International Application No. PCT/US2021/015787 dated May 27, 2021.
International Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 6, 2021.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027913 dated Jul. 12, 2021.
International Search Report and Written Opinion from International Application No. PCT/US2021/027917 dated Aug. 19, 2021.
Issue Notification for U.S. Appl. No. 14/952,591 dated Jul. 28, 2021.
Issue Notification for U.S. Appl. No. 29/624,661 dated Aug. 4, 2021.
Non-Final Office Action for U.S. Appl. No. 14/592,591 dated Mar. 20, 2020.
Non-Final Office Action for U.S. Appl. No. 16/452,145 dated Sep. 28, 2021.
Non-Final Office Action for U.S. Appl. No. 16/452,258 dated Sep. 28, 2021.
Non-Final Office Action for U.S. Appl. No. 16/478,180 dated Oct. 22, 2021.
Non-Final Office Action for U.S. Appl. No. 16/899,956 dated Sep. 2, 2021.
Non-Final Office Action for U.S. Appl. No. 16/904,868 dated Oct. 5, 2021.
Non-Final Office Action for U.S. Appl. No. 17/330,657 dated Aug. 11, 2021.
Notice of Allowance for U.S. Appl. No. 14/952,591 dated Jul. 8, 2021.
Notice of Allowance for U.S. Appl. No. 17/088,272 dated Aug. 5, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/260,103 filed Sep. 8, 2016.
U.S. Appl. No. 15/611,587, filed Jun. 1, 2017.
U.S. Appl. No. 16/245,726, filed Jan. 11, 2019.
U.S. Appl. No. 17/378,015, filed Jul. 16, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123 filed Sep. 8, 2021.
U.S. Appl. No. 17/461,036 mailed Aug. 30, 2021.
U.S. Appl. No. 29/741,751, filed Jul. 15, 2020.
Corrected Notice of Allowability for U.S. Appl. No. 17/330,657 dated Dec. 9, 2021.
Final Office Action for U.S. Appl. No. 16/452,145 dated Mar. 25, 2022.
Final Office Action for U.S. Appl. No. 16/904,868 dated Mar. 10, 2022.
International Search Report and Written Opinion from International Application No. PCT/US2021/024162 dated Jul. 8, 2021.
International Search Report and Written Opinion from International Application No. PCT/US2021/035181 dated Sep. 16, 2021.
International Search Report and Written Opinion from International Application No. PCT/US2021/043893 dated Nov. 22, 2021.
International Search Report and Written Opinion from International Application No. PCT/US2021/044699 dated Nov. 22, 2021.
International Search Report and Written Opinion from International Application No. PCT/US2021/045188 dated Jan. 26, 2022.
International Search Report and Written Opinion from International Application No. PCT/US2021/047536 dated Dec. 23, 2021.
International Search Report and Written Opinion from International Application No. PCT/US2021/048211 dated Dec. 22, 2021.
International Search Report and Written Opinion from International Application No. PCT/US2021/048661 dated Feb. 14, 2022.
International Search Report and Written Opinion from International Application No. PCT/US2021/056566 dated Feb. 11, 2022.
Non-Final Office Action for U.S. Appl. No. 16/245,726 dated Jan. 21, 2022.
Non-Final Office Action for U.S. Appl. No. 16/369,676 dated Mar. 31, 2022.
Non-Final Office Action for U.S. Appl. No. 16/449,039 dated Dec. 8, 2021.
Non-Final Office Action for U.S. Appl. No. 29/741,751 dated Jan. 18, 2022.
Notice of Allowance for U.S. Appl. No. 16/899,956 dated Dec. 29, 2021.
Notice of Allowance for U.S. Appl. No. 17/088,272 dated Mar. 4, 2022.
Notice of Allowance for U.S. Appl. No. 17/088,272 dated Nov. 24, 2021.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Parness, et al., "A microfabricated wedge-shaped adhesive array displaying gecko-like dynamic adhesion, directionality", J.R. Soc. Interface, 2009, pp. 1223-1232.
Tsipenyuk, et al., "Use of biomimetic hexagonal surface texture in friction against lubricated skin", Journal of the Royal Society—Interface, 2014, pp. 1-6.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-

(56) References Cited

OTHER PUBLICATIONS

Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Notice of Allowance for U.S. Appl. No. 17/330,657 dated Mar. 16, 2022.
Notice of Allowance for U.S. Appl. No. 17/330,657 dated Nov. 26, 2021.
Restriction Requirement for U.S. Appl. No. 16/433,773 dated Dec. 7, 2021.
Advisory Action for U.S. Appl. No. 16/904,868 dated Jun. 15, 2022.
Final Office Action for U.S. Appl. No. 16/452,258 dated Jun. 14, 2022.
Final Office Action for U.S. Appl. No. 16/478,180 dated Jun. 22, 2022.
International Search Report and Written Opinion for International Application No. PCT/US2022/019480 dated Jun. 13, 2022.
International Search Report and Written Opinion from International Application No. PCT/US2020/057562 dated Jan. 27, 2021.
International Search Report and Written Opinion from International Application No. PCT/US2021/026607 dated Jul. 29, 2021.
International Search Report and Written Opinion from International Application No. PCT/US2021/049404 dated Jan. 18, 2022.
International Search Report and Written Opinion from International Application No. PCT/US2021/051456 dated Jan. 19, 2022.
International Search Report and Written Opinion from International Application No. PCT/US2021/053593 dated Apr. 11, 2022.
International Search Report and Written Opinion from International Application No. PCT/US2021/055515 dated Jan. 28, 2022.
International Search Report and Written Opinion from International Application No. PCT/US2021/060993 dated Mar. 18, 2022.
International Search Report and Written Opinion from International Application No. PCT/US2021/062440 dated Mar. 28, 2022.
International Search Report and Written Opinion from International Application No. PCT/US2022/011108 dated Apr. 22, 2022.
International Search Report and Written Opinion from International Application No. PCT/US2022/011281 dated Apr. 25, 2022.
International Search Report and Written Opinion from International Application No. PCT/US2022/011419 dated Jun. 7, 2022.
International Search Report and Written Opinion from International Application No. PCT/US2022/011421 dated Jun. 13, 2022.
International Search Report and Written Opinion from International Application No. PCT/US2022/012794 dated May 3, 2022.
International Search Report and Written Opinion from International Application No. PCT/US2022/015471 dated May 16, 2022.
International Search Report and Written Opinion from International Application No. PCT/US2022/016942 dated Jun. 3, 2022.
International Search Report and Written Opinion from International Application No. PCT/US2022/018170 dated May 31, 2022.
International Search Report and Written Opinion from International Application No. PCT/US2022/019254 dated Jun. 7, 2022.
International Search Report and Written Opinion from International Application No. PCT/US2022/021103 dated Jun. 23, 2022.
Issue Notification for U.S. Appl. No. 17/088,272 dated Jun. 15, 2022.
Issue Notification for U.S. Appl. No. 17/330,657 dated Jun. 22, 2022.
Non-Final Office Action for U.S. Appl. No. 16/433,773 dated Apr. 21, 2022.
Non-Final Office Action for U.S. Appl. No. 17/662,700 dated Jul. 22, 2022.
Notice of Allowance for U.S. Appl. No. 16/899,956 dated Apr. 19, 2022.
Notice of Allowance for U.S. Appl. No. 29/741,751 dated Jun. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 62/923,279, filed Oct. 18, 2019.
U.S. Appl. No. 62/926,767, filed Oct. 28, 2019.
U.S. Appl. No. 62/967,158, filed Jan. 26, 2020.
U.S. Appl. No. 63/008,112, filed Apr. 10, 2020.
U.S. Appl. No. 63/094,646, filed Oct. 21, 2020.
U.S. Appl. No. 63/191,558, filed May 21, 2021.
U.S. Appl. No. 63/192,289, filed May 24, 2021.
U.S. Appl. No. 63/230,897, filed Aug. 9, 2021.

\* cited by examiner

FLUID COLLECTION GARMENTS

CROSS-REFERENCE TO RELATED APPLICATIONS

This application is a continuation of PCT International Application No. PCT/US19/29613 filed Apr. 29, 2019, which application claims priority from U.S. Provisional Application No. 62/665,335 filed on 1 May 2018, the disclosure of each of which are incorporated herein, in their entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments disclosed herein are related to garments carrying fluid collection devices and methods of using fluid collection device containing garments.

In an embodiment, a fluid collection garment is disclosed. The fluid collection garment includes a garment configured to be worn on the pelvis of a subject, the garment having a port configured to be positioned about a urethral region on the pelvis of the subject when the garment is worn. The fluid collection garment includes a fluid collection device sized and shaped to fit within the port. The fluid collection device includes a fluid impermeable barrier at least partially defining a chamber, the fluid impermeable barrier also defining an opening extending therethrough, the opening configured to be positioned adjacent to a female urethra or have a male urethra positioned therethrough. The fluid collection device includes wicking material disposed with the chamber. The fluid collection device includes a conduit disposed within wicking material, the conduit including an inlet positioned within the fluid collection device and an outlet configured to be in fluid communication with a vacuum source.

In an embodiment, a fluid collection system is disclosed. The fluid collection system includes a fluid storage container configured to hold a fluid. The fluid collection system includes a garment including a port therein. The fluid collection system includes a fluid collection device sized and configured to the disposed within the port and in fluid communication with the fluid storage container. The fluid collection device includes a fluid impermeable barrier at least partially defining a chamber, the fluid impermeable barrier also defining an opening extending therethrough, the opening configured to be positioned adjacent to a female urethra or have a male urethra positioned therethrough. The fluid collection device includes a wicking material disposed with the chamber. The fluid collection device includes a conduit disposed within wicking material, the conduit including an inlet positioned within the fluid collection device and an outlet. The fluid collection system includes a vacuum source in fluid communication with one or more of the fluid storage container or the outlet of the fluid collection device, the vacuum source configured to draw fluid from the fluid collection device In an embodiment, a method to collect fluid is disclosed. The method includes positioning a fluid collection device in a port of a garment, the port being sized and positioned on the garment to align an opening of the fluid collection device with a urethra of a wearer of the garment. The method includes disposing the garment on the wearer such that the fluid collection device is positioned adjacent to the urethra of the wearer. The method includes receiving fluids from the urethra into a chamber of the fluid collection device.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to garments carrying fluid collection devices and methods of using the same. The garments include a port (e.g., pocket) sized and positioned to retain a fluid collection device therein. The garments carry at least one fluid collection device sized to at least partially fit within the port. The port is positioned on the garment to align the fluid collection device therein with one or more anatomical structures (e.g., urethra) of the wearer when the garment is worn.

In some examples, the garment includes a material in the region of the port that allows fluids to readily pass therethrough to the fluid collection device therein. The fluid collection devices include a fluid impermeable barrier that at least partially defines a chamber therein. The fluid impermeable barrier also defines an opening extending therethrough that is configured to be positioned adjacent to a female urethra or have a male urethra positioned therethrough. The fluid collection device includes a conduit for removing fluid from the chamber. The conduit includes an inlet in fluid communication with (e.g., positioned within) the chamber of the fluid collection device and an outlet configured to be in fluid communication with (e.g., fluidly coupled to) a vacuum source or fluid storage container. The fluid collection device also include a tube having a channel extending between an inlet and outlet thereof. The inlet is configured to be in fluid communication with the vacuum source and the outlet is configured to be in fluid communication with a fluid storage (vessel or container), or vice versa. The outlet is positioned downstream from the inlet.

The garments disclosed herein are configured to collect fluids from an individual. The fluids collected by the garments (e.g., fluid collection devices therein) can include urine. The fluids collected by the fluid collection devices can also include at least one of vaginal discharge, penile discharge, reproductive fluids, blood, sweat, or other bodily fluids. The fluid collection garments, systems, and methods disclosed herein can help keep a wearer dry and sanitary while reducing or eliminating the need for more invasive means of collecting fluid emissions such as catheterization.

Figure 1:
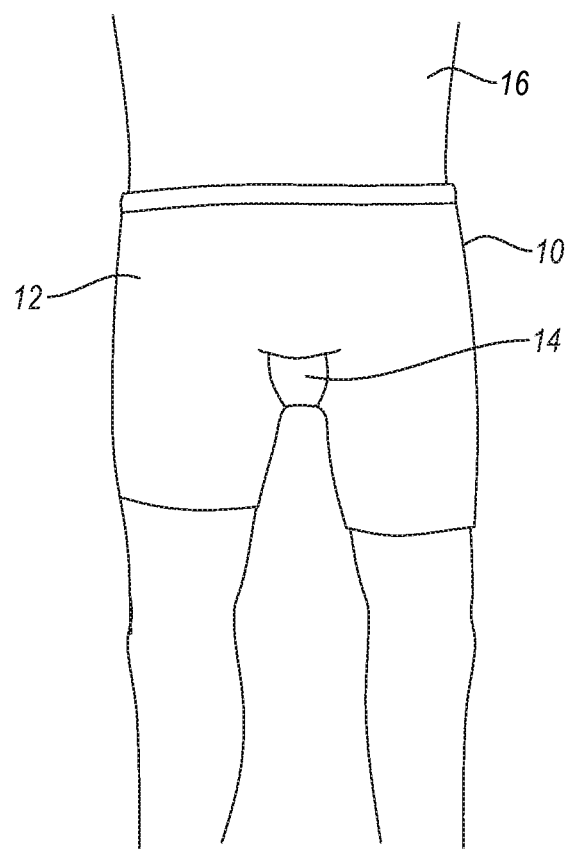
FIG. 1 is a front view of a garment for fluid collection, according to an embodiment.

FIG. 1 is a front view of a garment 10 for fluid collection, according to an embodiment. The garment 10 includes a fabric body 12 that is sized and shaped to fit on a pelvis of a wearer 16 and maintain position thereon. The fabric body 12 of the garment 10 includes a port 14 therein. The port 14 may be positioned in the crotch of the fabric body 12 (e.g., a position corresponding to the crotch of the wearer 16 when the garment 10 is worn). The crotch of the garment can include the region of the garment positioned to cover an area extending from the pubic region to the anus or the perineum of the subject when the garment is worn. The port 14 is positioned over at least the region of the urethra of the wearer 16 (e.g., within the region of the crotch) when the garment 10 is worn. A fluid collection device (not shown) may be disposed within the port 14, such that fluids in the region, such as urine, may be collected by the fluid collection device. Accordingly, the garment 10 may serve to align the fluid collection device with the urethra of the user such that fluids originating therefrom can be collected before soiling clothing or bedding.

The fabric body 12 may include one or more of natural materials such as cotton, wool, silk, rubber, etc. or synthetic materials such as polyamides (e.g., NYLON), poly(ethylene terephthalate), beta-1,4-Glucan-4-Glucanohydrolase (e.g., Rayon), polyester, silicone, a polyether-polyurea copolymer (e.g., SPANDEX), olefin fibers, acrylic fibers, etc. In some examples, the fabric body includes one or more of a mesh fabric, a woven fabric, or a non-woven material. The fabric body 12 can be shaped as a garment, such as an undergarment, pants, shorts, a jock-strap, adjustable versions of any of the foregoing, or analogues of any of the foregoing. In such examples, stitching, buttons, snaps, or other fasteners can join a plurality of panels which collectively form the garment.

In examples, the fabric body 12 may include a discrete portion of fabric or a gap therein to allow fluid to flow through the fabric body 12. For example, the fabric body 12 may be an undergarment and the crotch of the undergarment can include a mesh fabric or one or more gaps therein such that urine emitted from the wearer can pass through the fabric body 12. In examples, the fabric body 12 can include one or more portions which include a relatively soft fabric and one or more portions that include a relatively rough fabric. For example, the fabric body 12 can include a cotton gusset and a nylon body.

The port 14 may be arranged as a pocket on or in the fabric body 12. The port 14 may be positioned on the fabric body 12 such that the port 14 is located about a urethral region on the pelvis of the subject when the garment 10 is worn. For example, the port 14 can be positioned over or in the crotch of the fabric body 12. The port 14 can receive and retain a fluid collection device therein. The port 14 may be a separate portion of fabric affixed on at least two sides (e.g., three or four) to the fabric body 12 to form a pocket. The port 14 may include an excess amount of fabric when no fluid collection device is positioned therein, to accommodate a fluid collection device. For example, the port 14 may be sized and shaped to accommodate a female fluid collection device or a male fluid collection device, such as any of those disclosed herein. The port 14 may be adjustable to accommodate the female fluid collection device or the male fluid collection device depending on the amount of fabric forming the port 14, such as due to adjustments (e.g., tightening a drawstring or straps). The port 14 may be sown on or in the fabric body 12. The port 14 may be integrally formed in the fabric body 12 (e.g., weaved into the fabric body 12).

The port 14 may be releasably attachable to the fabric body 12. For example, the port 14 may be affixed to the fabric body by hook and loop fasteners, buttons, snaps, a zipper, magnets, or any other fastener. In such examples, the fabric body 12 can include a male portion of the snap connection, a hook strip, a button, or a magnet disposed in the region around the crotch of the subject, such as around the periphery of the region where a urethra of a wearer may be located while the garment is worn. The piece of fabric defining the port 14 can include a female portion of the snap connection, a loop strip, a button-hole, or a magnet disposed about a periphery of the piece of fabric. In such examples, the port 14 can be aligned and retained on the fabric body 12 by the snap connection, hook strip, button, or magnet. Accordingly, the port 14 can be removed and replaced, such as to insert, replace, clean, or otherwise service the fluid collection device in the garment. The port 14 may include partial sealing devices to retain the urine collection device there, such as a draw string, snaps, hook and loop fasteners, etc. For example, the port 14 can include a temporarily sealable structure such as hook and loop fasteners at a top portion to allow a user to insert and remove a urine collection device and to allow the user to seal the urine collection device within the port 14. In some examples, the urine collection device may be retained within the port 14 via pressure exerted thereon by a stretchable material used to form the port 14.

A fluid collection device can be disposed in the garment 10 (e.g., in the port 14). For example, the port 14 may be sized and shaped to accommodate a female fluid collection device or a male fluid collection device, such as any of those disclosed herein.

In some examples (not shown), the port may 14 may not form a pocket. In such examples, the garment may include fasteners for securing the fluid collection device in a location on the garment configured to fit on or over an anatomical feature (e.g., urethra) of the wearer. For example, the port may include snaps, hook-and-loop fasteners, or the like in the crotch of the garment for attaching to corresponding fasteners on a fluid collection device.

Figure 2A:
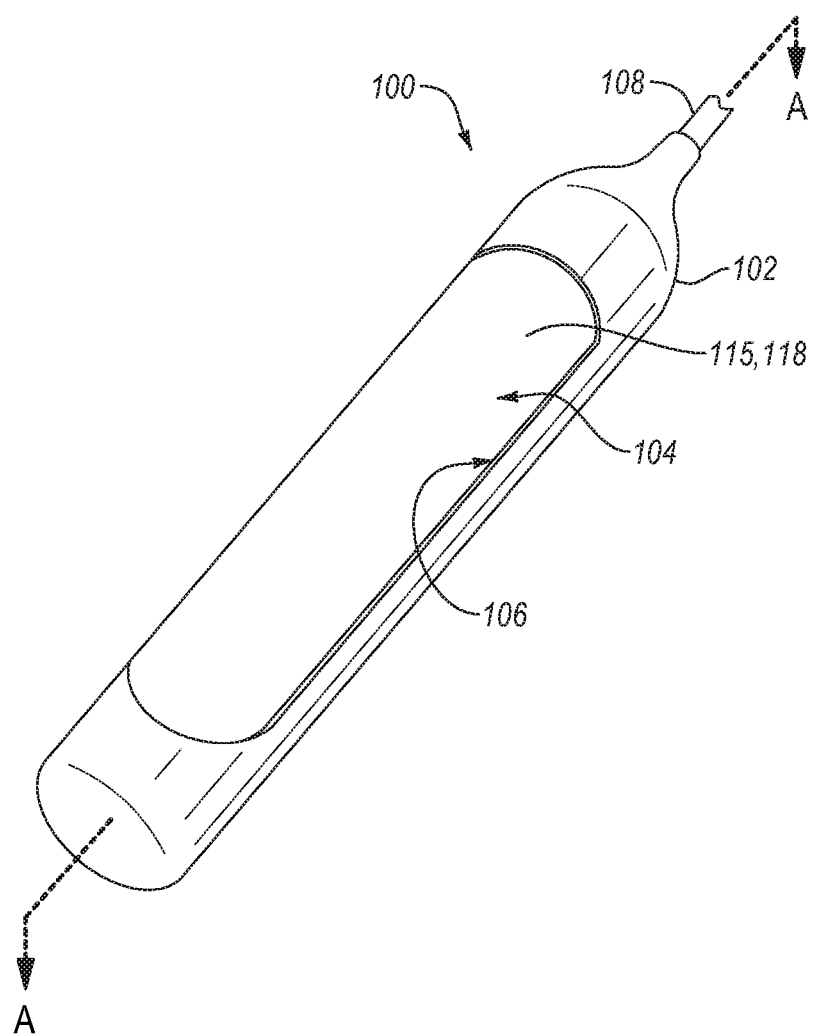
FIG. 2A is an isometric view of a fluid collection device, according to an embodiment.
Figure 2B:
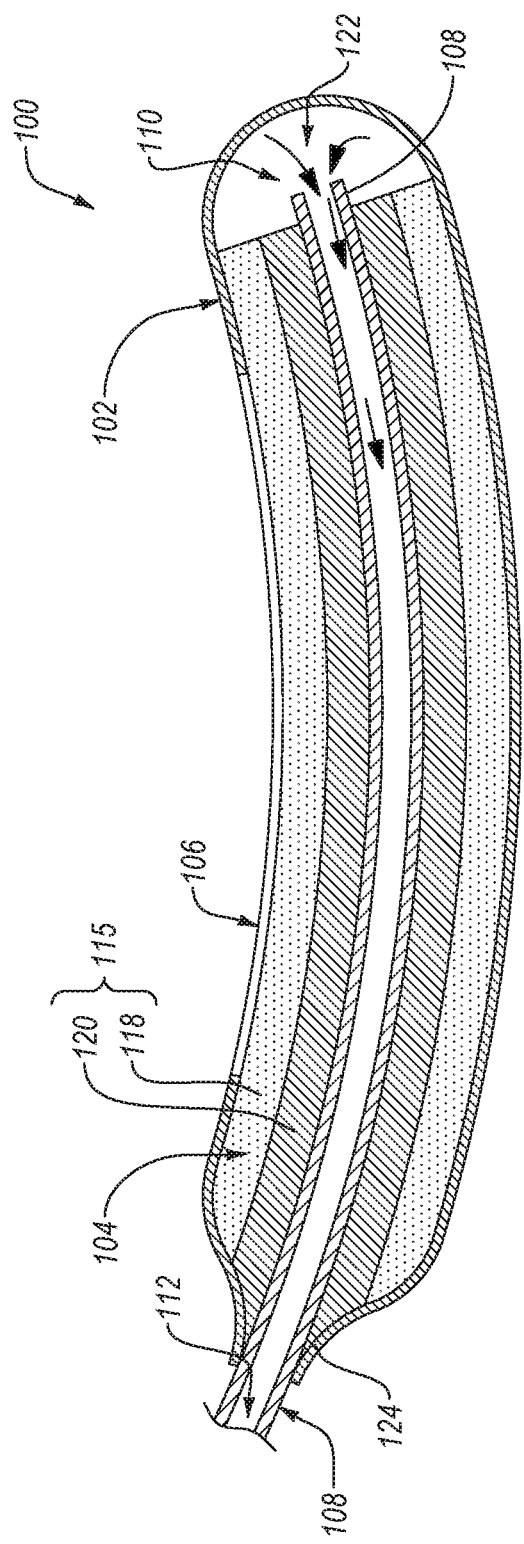
FIG. 2B is a cross-sectional view of the fluid collection device of FIG. 2A taken along the plane A-A, according to an embodiment.

FIG. 2A is an isometric view of a fluid collection device, according to an embodiment. FIG. 2B is a cross-sectional view of the fluid collection device of FIG. 2A taken along the plane A-A, according to an embodiment. Reference to both FIGS. 2A and 2B is made below.

The fluid collection device 100 may be substantially cylindrical, ellipsoid, prismatic, or any other shape suitable for complementing or contouring to the vaginal region of a female subject. The fluid collection device 100 may include a fluid impermeable barrier 102, wicking material 115, and a conduit 108. The wicking material 115 may be disposed within the fluid impermeable barrier 102. The conduit 108 may be at least partially disposed within the wicking material 115.

The fluid impermeable barrier 102 at least partially defines at least a portion of an outer surface of the fluid collection device 100. The fluid impermeable barrier 102 at least partially defines a chamber 104 therein (e.g., interior region of the fluid collection device 100) and an opening 106. The opening 106 is formed in and extends through the fluid impermeable barrier 102 thereby enabling fluids to enter the chamber 104 from outside of the fluid collection device 100. The opening 106 can be configured to be positioned adjacent to a female urethra, such as on or between the labia majora of a female user.

The fluid impermeable barrier 102 may also temporarily retain or store fluids in the chamber 104. For example, the fluid impermeable barrier 102 can be formed of any suitable fluid impermeable materials, such as a fluid impermeable polymer (e.g., silicone, polypropylene, polyethylene, polyethylene terephthalate, polyurethane, a polycarbonate, polyvinyl chloride, latex, silicone, etc.), a metal film, another suitable material, or combinations thereof. As such, the fluid impermeable barrier 102 may prevent at least some of the fluid(s) from exiting the portions of the chamber 104 that are spaced from the opening 106.

The fluid impermeable barrier 102 can be air permeable and fluid impermeable. In such an example, the fluid impermeable barrier 102 can be formed of a hydrophobic material that defines a plurality of pores. In an example, at least one or more portions of an outer surface of the fluid impermeable barrier 102 can be formed from a soft and/or smooth material thereby reducing chafing of the skin of the user. The fluid impermeable barrier 102 may include markings thereon, such as one or more markings to aid a user in aligning the device 100 on the wearer. For example, a line on the fluid impermeable barrier 102 (e.g., opposite the opening 106) may allow a healthcare professional to align the opening 106 over the urethra of the wearer. In examples, the markings may include one or more of alignment guide or an orientation indicator, such as a stripe or hashes. Such markings may be positioned to align the device 100 to one or more anatomical features such as a pubic bone, etc.

The wicking material 115 may be disposed within the fluid impermeable barrier 102. The wicking material 115 may include permeable material designed to wick or pass fluid therethrough. The permeable properties referred to herein can be wicking, capillary action, diffusion, or other similar properties or processes, and are referred to herein as "permeable" and/or "wicking." Such "permeation" or "wicking" may not include absorption into the permeable or wicking material. The wicking material 115 may collect the fluid that travels through the opening 106. By not using absorbent materials, the wicking material 115 may facilitate the movement of fluid(s) through the opening 106 into the chamber 104 without retaining the fluid(s) in the wicking material 115. Accordingly, the device 100 may provide a dry interface with a wearer even after fluids have been wicked from the wearer into the chamber 100. The wicking material 115 may include more than one material, such as a plurality of materials. The plurality of materials may include a plurality of layers concentrically disposed within one another. The concentrically disposed layers of wicking materials may exhibit a gradient of wicking, such as where the innermost wicking material includes the greatest or least wicking ability of the plurality of materials.

In examples, the wicking material 115 may include one or more of a fluid permeable support 120 (FIG. 2B) or a fluid permeable membrane 118. For example, the fluid collection device 100 can include a fluid permeable membrane 118 disposed in the chamber 104. The fluid permeable membrane 118 can cover at least a portion (e.g., all) of the opening 106. The fluid permeable membrane 118 can be configured to wick any fluid away from the opening 106 thereby preventing the fluid from escaping the chamber 104. The fluid permeable membrane 118 can also wick the fluid generally towards an interior of the chamber 104, as discussed in more detail below. The fluid permeable membrane 118 can include any material that can wick the fluid. The fluid permeable membrane 118 may be a wicking material that is non-absorbent. For example, the fluid permeable membrane 118 can include fabric, such as a gauze (e.g., a silk, linen, or cotton gauze), woven fabrics (e.g., tricot, etc.), natural fibers (e.g., wool, etc.), synthetic fibers (e.g., polyester, Nylon, polypropylene, Spandex, etc.), treated fabrics (e.g., cotton, silk, linen, or any other fabric that has been chemically treated with one or more of a hydrophobic agent or a hydrophilic agent to move fluid away from the skin), any other soft fabric, or any other smooth fabric. In some examples, the fluid permeable membrane 118 can include an open cell foam, such as a foam formed from any of the fluid permeable membrane materials 118 disclosed above and which wicks fluid. The foam may be a thin layer of foam. Forming the fluid permeable membrane 118 from gauze, soft and/or smooth fabric, or soft/smooth foam can reduce chafing caused by the fluid collection device 100 rubbing against the skin of a user.

The fluid collection device 100 can include a fluid permeable support 120 (FIG. 2B) disposed in the chamber 104. The fluid permeable support may support the fluid permeable membrane 118 since the fluid permeable membrane 118 can be formed from a foldable, flimsy, or otherwise easily deformable material. For example, the fluid permeable support can be positioned such that the fluid permeable membrane 118 is disposed between the fluid permeable support and the fluid impermeable barrier 102. As such, the fluid permeable support can support and maintain the position of the fluid permeable membrane 118. The fluid permeable support can be formed from any fluid permeable material that is less deformable than the fluid permeable membrane 118. For example, the fluid permeable support 120 can include a porous nylon structure or an open cell foam. In some examples, the fluid permeable support 120 can be omitted from the fluid collection device 100.

In some examples, the wicking material 115 (e.g., one or more of the fluid permeable membrane 118 or the fluid permeable support 120) can at least substantially completely fill portions of the chamber 104 that are not occupied by the conduit 108. For example, the wicking material 115 may fill the portions of the chamber 104 that are not occupied by the conduit 108. In some examples, the fluid permeable membrane 118 and the fluid permeable support may not substantially completely fill the portions of the chamber 104 that are not occupied by the conduit 108. In such examples, the fluid collection device 100 may include the reservoir 122 (e.g., void space) disposed in the chamber 104. The reservoir 122 may include a void space defined between the wicking material in the chamber 104 and the interior surface of the fluid impermeable barrier 102. At least some of the fluid wicked by the wicking material 115 may drain out of the wicking material 115 and collect in the reservoir 122.

The fluid collection device 100 may also include conduit 108 that is at least partially disposed in the chamber 104. The conduit 108 may be disposed within the wicking material and includes an inlet positioned within the fluid collection device 100 and an outlet configured to be in fluid communication with a vacuum source. The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In examples, the conduit 108 may include silicon or latex. The conduit 108 (e.g., a tube) includes an inlet at a first end region and an outlet at a second end region positioned downstream from the inlet. The conduit 108 fluidly couples (e.g., places the components in fluid communication with) an interior region of the chamber 104 with a fluid storage container or a vacuum source for removing fluids from the fluid collection device 100. The fluid may be removed from the chamber 104 via the conduit 108. As suction or vacuum force is applied or formed in the conduit 108 by the vacuum source (FIG. 8), the fluid in the chamber 104 may be drawn into the inlet and out of the fluid collection device 100 via the conduit 108.

In some examples, the inlet of the conduit 108 may be disposed in an innermost or gravimetrically low spot in the chamber 104. For example, the conduit 108 may extend far enough into the chamber 104 to position the inlet in a gravimetrically low spot of the chamber 104 (e.g., fluid reservoir within the interior of the fluid collection device 100).

The fluid collection device 100 and components thereof may be deformable (e.g., bendable) responsive to pressure applied thereto. For example, the fluid collection device 100 and the components thereof may bend to conform to the surface(s) of the body of the user, such as when disposed between a garment and the user. One or more portions of the fluid collection device 100 may be resiliently deformable to at least partially contour to the body of the user when worn. In examples, the fluid collection device 100 may bend when disposing proximate to the urethra (e.g., between the labia) when garments the fluid collection device 100 are positioned on a wearer (e.g., user). In such examples, the longitudinal ends of the fluid collection device 100 may bend out of axial alignment with a central portion of the fluid collection device 100.

The fluid collection device 100 is an example of a female fluid collection device 100 sized, shaped, and otherwise configured to receive fluids from a female user. The opening 106 can be configured to be positioned adjacent to a female urethra. The opening 106 can be positioned on an upward or inward-facing (e.g., toward a user) portion of the fluid collection device 100. The conduit 108 (e.g., a tube) includes an inlet 110 at a first end region and an outlet 112 at a second end region positioned downstream from the inlet 110. The conduit 108 fluidly couples the chamber 104 with a fluid storage container (not shown) or a vacuum source (not shown).

In the illustrated example, the conduit 108 is at least partially disposed in the chamber 104. For example, the conduit 108 may extend into the fluid impermeable barrier 102 from the first end region (e.g., proximate to the outlet 112) and may extend to the second end region (e.g., opposite the first end region) to a point proximate to the reservoir 122 such that the inlet 110 is in fluid communication with the reservoir 122. In some examples (not shown), the conduit 108 may enter the second end region and the inlet 110 of the conduit 108 may be disposed in the second end region (e.g., in the reservoir 122). The fluid collected in the fluid collection device 100 may be removed from the interior region of the chamber 104 via the conduit 108. The conduit 108 may include a flexible material such as plastic tubing (e.g., medical tubing) as disclosed herein. In some examples, the conduit 108 may include one or more portions that are resilient, such as to by having one or more of a diameter or wall thickness that allows the conduit to be flexible. In some examples, the inlet 110 may not extend into the reservoir 122. In such examples, the inlet 110 may be disposed within the wicking material or a terminal end thereof.

The fluid collection device 100 may be positioned proximate to the female urethra (e.g., on or between the labia) and urine may enter the chamber 104 of the fluid collection device 100 via the opening 106. The fluid collection device 100 receives the fluids into the chamber 104 via the opening 106. For example, the opening 106 can exhibit an elongated shape that is sized and positioned to extend from a first location below the urethral opening (e.g., at or near the anus or the vaginal opening) to a second location above the urethral opening (e.g., at or near the clitoris or the mons pubis). The opening 106 can exhibit an elongated shape since the space between the legs of a female is relatively small when the legs of the female wearer are closed, thereby only permitting the flow of the fluids along a path that corresponds to the elongated shape of the opening 106. The opening 106 in the fluid impermeable barrier 102 can exhibit a width that is measured transverse to the longitudinal direction of the fluid collection device 100 and may be at least about 10% of the circumference of the fluid collection device 100, such as about 25%, 30%, 40%, 50%, 60%, 75%, 85%, 100% or ranges between any combination of the foregoing, of the circumference of the fluid collection device 100. The opening 106 can exhibit a width that is greater than 50% of the circumference of the fluid collection device 100 since the vacuum (e.g., suction) through the conduit 108 pulls the fluid into the conduit 108. In an example, one or more portions of the fluid impermeable barrier 102 can be configured to be attached to the garment, such as adhesively attached (e.g., with a hydrogel adhesive, such as a hydrogel layer, such as those disclosed in U.S. Patent Application Publication No. 2017/0189225, the disclosure of which is incorporated herein by reference in its entirety) or mechanically attached (e.g., hook and loop fasteners, buttons, snaps, etc.). In some examples, the opening 106 may be vertically oriented (e.g., having a major axis parallel to the longitudinal axis of the fluid collection device 100). In some examples, (not shown), the opening 106 may be horizontally oriented (e.g., having a major axis perpendicular to the longitudinal axis of the device 100). The longitudinal axis or dimension of the fluid collection devices disclosed herein refers to the axis or dimension that is the largest dimension of the device, such as axially along a cylindrical device as show in FIG. 2A.

As shown in FIG. 2B, the wicking material 115 may include one or more of the fluid permeable membrane 118 and the fluid permeable support 120, each disposed in the chamber 104. The fluid permeable membrane 118 can cover at least a portion (e.g., all) of the opening 106. The fluid permeable membrane 118 is configured to wick any fluid away from the opening 106 thereby preventing the fluid from escaping the chamber 104. The fluid permeable membrane 118 can also wick the fluid generally towards an interior of the chamber 104, such as due to a pressure differential provided by a vacuum or gradient of increasingly strong wicking material(s) (e.g., stronger wicking ability in the fluid permeable support 120 than the fluid permeable membrane 118). The wicking material 115 may be non-absorbent.

The fluid permeable support 120 may be disposed in the chamber 104, such as concentrically within the fluid permeable membrane 118. The fluid permeable support 120 may be formed from material that is more rigid (e.g., less deformable) than the material in the fluid permeable membrane 118, such as a stiffer material or a denser material. The fluid permeable support 120 may include a material that wicks fluids but is non-absorbent. The fluid permeable support 120 may include any of the materials disclosed herein for the fluid permeable membrane 118. For example, the fluid permeable support 120 can include a porous nylon structure. The fluid permeable support 120 is sized and shaped to support the fluid permeable membrane 118 since the fluid permeable membrane 118 can be formed from a foldable, flimsy, or otherwise relatively easily deformable material. For example, the fluid permeable support 120 can be positioned such that the fluid permeable membrane 118 is disposed between the fluid permeable support 120 and the fluid impermeable barrier 102. As such, the fluid permeable support 120 can support and maintain the position of the fluid permeable membrane 118 while also wicking fluid therefrom into the chamber 104 to be removed from the fluid collection device 100. In some examples, the fluid permeable support 120 may be formed of a relatively higher wicking material that the fluid permeable membrane 118. The fluid permeable support 120 can be omitted from some examples of the fluid collection device 100.

In some examples, the fluid permeable membrane 118 and the fluid permeable support 120 at least substantially completely fill the portions of the chamber 104 that are not occupied by the conduit 108. In another example, the fluid permeable membrane 118 and the fluid permeable support 120 may not substantially completely fill the portions of the chamber 104 that are not occupied by the conduit 108. In such an example, the fluid collection device 100 includes the reservoir 122. The reservoir 122 is a substantially unoccupied portion of the chamber 104. The fluids that are in the chamber 104 can flow through the fluid permeable membrane 118 and/or fluid permeable support 120 to the reservoir 122. The reservoir 122 can store at least some of the fluids therein. For example, the fluid impermeable barrier 102 can store fluids in the reservoir 122. The reservoir 122 may be disposed in any portion of the interior region of the chamber 104. For example, the fluid reservoir 122 may be positioned in the second end region of the chamber 104.

The reservoir 122 can be located at the portion of the chamber 104 that is closest to the inlet 110 (e.g., the second end region). However, the reservoir 122 can be located at different locations in the chamber 104. For example, the reservoir 122 can be located at the end of the chamber 104 that is closest to the outlet 112. In another example, fluid collection device 100 can include multiple reservoirs, such as a first reservoir that is located at the portion of the chamber 104 that is closest to the inlet 110 (e.g., second end region) and a second reservoir that is located at the portion of the of the chamber 104 that is closest to the outlet 112 (e.g., first end region). In another example, the fluid permeable support 120 is spaced from at least a portion of the conduit 108 and the reservoir 122 can be the space between the fluid permeable support 120 and the conduit 108.

In some examples, the fluid collection device 100 may be substantially cylindrical, ellipsoid, prismatic, or any other shape suitable for complementing or contouring to the vaginal region of a female subject. The cross-sectional shape of the fluid collection devices disclosed herein may include any of various shapes or sizes. For example, the cross-sectional shape (transverse to the longitudinal axis) may be substantially round (e.g., circular), elliptical, rectangular, triangular, irregular (e.g., having no specific shape), etc.

Other examples of fluid impermeable barriers, fluid permeable membranes, fluid permeable supports, chambers, and their shapes and configurations are disclosed in U.S. patent application Ser. No. 15/611,587 filed on Jun. 1, 2017 and U.S. patent application Ser. No. 15/260,103 filed on Sep. 8, 2016 (published as US 2016-0374848 on Dec. 29, 2016), the disclosure of each of which is incorporated herein, in its entirety, by this reference.

The fluid impermeable barrier 102, the fluid permeable membrane 118 and the fluid permeable support 120 can be configured to have the conduit 108 at least partially disposed in the chamber 104. For example, at least one of the fluid permeable membrane 118 and the fluid permeable support 120 can be configured to form a space that accommodates the conduit 108. In another example, the fluid impermeable barrier 102 can define an aperture 124 sized to receive the conduit 108 (e.g., at least one tube). The at least one conduit 108 can be disposed in the chamber 104 via the aperture 124. The aperture 124 can be configured to form an at least partially fluid tight seal against the conduit 108 or the at least one tube thereby substantially preventing the fluids from escaping the chamber 104. In some examples, the aperture 124 may be disposed on the second end region nearer the reservoir 122. In such examples, the conduit 108 may be disposed in only the second end region with the inlet 110 being disposed in the second end region (e.g., the reservoir 122).

As previously discussed, the conduit 108 is configured to be in fluid communication with, and at least partially extend between, one or more of the fluid storage container (not shown) and the vacuum source (not shown). In an example, the conduit 108 is configured to be directly connected to the vacuum source (not shown). In such an example, the conduit 108 can extend from the fluid impermeable barrier 102 by at least one foot, at least two feet, at least three feet, or at least six feet. In another example, the conduit 108 is configured to be indirectly connected or in fluid communication with at least one of the fluid storage container (not shown) and the vacuum source (not shown). In some examples, the conduit is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 110 and the outlet 112 are sized, positioned, or otherwise configured to fluidly couple (e.g., directly or indirectly) the vacuum source (not shown) to the chamber 104 (e.g., the reservoir 122). In an example, the inlet 110 and/or the outlet 112 can form a male connector. In another example, the inlet 110 and/or the outlet 112 can form a female connector. In an example, the inlet 110 and/or the outlet 112 can include ribs that are configured to facilitate secure couplings. In an example, the inlet 110 and/or the outlet 112 can form a tapered shape. In an example, the inlet 110 and/or the outlet 112 can include a rigid or flexible material.

Locating the inlet 110 at or near a gravimetrically low point of the chamber 104 enables the conduit to receive more of the fluids than if inlet 110 was located elsewhere and reduce the likelihood of pooling (e.g., pooling of the fluids can cause microbe growth and foul odors). For instance, the fluids in the fluid permeable membrane 118 and the fluid permeable support 120 can flow in any direction due to capillary forces. However, the fluids may exhibit a preference to flow in the direction of gravity, especially when at least a portion of the fluid permeable membrane 118 and/or the fluid permeable support 120 is saturated with the fluids.

As the vacuum source (FIG. 8) applies a vacuum/suction in the conduit 108, the fluid(s) in the chamber 104 (e.g., at the second end region such as in the reservoir 122) may be drawn into the inlet 110 and out of the fluid collection device 100 via the conduit 108.

In an example, the conduit 108 is configured to be at least insertable into the chamber 104. In such an example, the conduit 108 can include one or more markers (not shown) on an exterior thereof that are configured to facilitate insertion of the conduit 108 into the chamber 104. For example, the conduit 108 can include one or more markings thereon that are configured to prevent over or under insertion of the conduit 108, such as when the conduit 108 defines an inlet 110 configured to be disposed in or adjacent to the reservoir 122. In another example, the conduit 108 can include one or more markings thereon that are configured to facilitate correct rotation of the conduit 108 relative to the chamber 104. In an example, the one or more markings can include a line, a dot, a sticker, or any other suitable marking. In some examples, the conduit may be frosted or opaque (e.g., black) to obscure visibility of the fluids therein.

In an example, one or more components of the fluid collection device 100 can include an antimicrobial material, such as an antibacterial material where the fluid collection device may contact the wearer or the bodily fluid of the wearer. The antimicrobial material can include an antimicrobial coating, such as a nitrofurazone or silver-containing coating. The antimicrobial material can inhibit microbial growth, such as microbial growth due to pooling or stagnation of the fluids. In an example, one or more components (e.g., impermeable barrier 102, conduit 108, etc.) of the fluid collection device 100 can include an odor blocking or absorbing material such as a cyclodextrine containing material or a thermoplastic elastomer (TPE) polymer.

Figure 3:
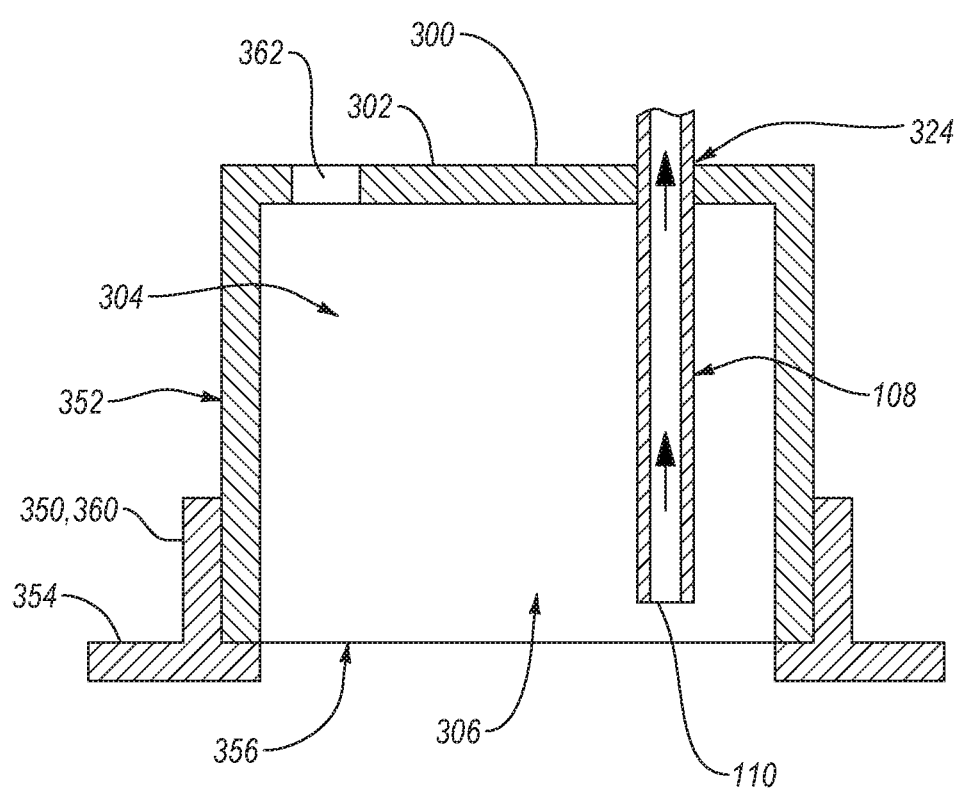
FIG. 3 is a cross-sectional view of a fluid collection device, according to an embodiment.

FIG. 3 is a cross-sectional view of a fluid collection device, according to an embodiment. Referring to FIG. 3, the fluid collection device 300 includes a receptacle 350 and a cup portion 352 (e.g., cup shaped container). The receptacle 350 is sized, shaped, and made of a material to be positioned on skin that surrounds the male urethra and have the male urethra positioned therethrough. For example, the receptacle 350 can include an annular base 354 that defines an opening 356 in the receptacle 350. The annular base 354 is sized and shaped to be positioned around the male urethra (e.g., positioned around the penis) and the opening 356 can be configured to have the male urethra positioned therethrough. The annular base 354 can also be sized, shaped, made of a material, or otherwise configured to be coupled to (e.g., adhesively attached, such as with a hydrogel adhesive) or disposed in the garment around the male urethra (e.g., around the penis). In some examples, the annular base 354 can exhibit the general shape of the skin surface that the annular base 354 is selected to be positioned on or coupled with and/or can be resiliently deformable or otherwise flexible thereby allowing the annular base 354 to conform to any shape of the skin surface. The receptacle 350 also defines a hollowed region that is configured to receive (e.g., seal against) the cup portion 352. For example, the receptacle 350 can include a flange 360 that extends upwardly from the annular base 354. The flange 360 may be tall enough to prevent the cup portion 352 from being accidentally removed from the receptacle 350 (e.g., at least 0.5 cm tall, 1 cm tall, at least 2 cm tall, or at least 5 cm tall). The flange 360 may be permanently or removably attached to the annular base 354, such as via mechanically locking, threading, interference fit, fasteners, adhesive, or the like. In some examples, the annular base 354 is optional. For example, the receptacle 350 may only include the flange 354. In some examples (not shown), the fluid collection device may have a one piece design, with the cup portion 352 and the receptacle 350 being a single piece. In some examples, the receptacle 350 is optional.

The cup portion 352 includes (e.g., may be formed from) a fluid impermeable barrier 302 that is sized and shaped to fit into the hollowed region of the receptacle 350. The cup portion 352 is shaped to retain a fluid therein. For example, the fluid impermeable barrier 302 may define the cup portion 352, such as forming a substantially tubular (e.g., cylindrical) body having an enclosed end as illustrated in FIG. 3. The cup portion 352 is sized and shaped to fit over the urethra of a male user, such as over the penis of a male wearing the device. Accordingly, the cup portion 352 may have a generally cupped shape with a chamber 304 therein. The fluid impermeable barrier 302 may be similar or identical to the fluid impermeable barrier 102, in one or more aspects. The fluid impermeable barrier 302 partially defines the chamber 304. The fluid impermeable barrier 302 may also define an opening 306 extending through the fluid impermeable barrier 302 that is configured to have a male urethra positioned therethrough. The fluid impermeable barrier 302 may also include at least one passageway 362 that allows the chamber 304 to remain substantially at atmospheric pressure. The passageway 362 may be disposed on any portion of the cup portion 352, such as a portion not intended to serve as a reservoir for collected fluids. The cup portion 352 also includes at least a portion of the conduit 108 therein, such as at least partially disposed in the chamber 304. For example, the conduit 108 may extend from the cup portion 352 to a region at least proximate to the opening 356. The region proximate to the opening 356 may be disposed near or on the skin around the male urethra (e.g., on the penis). Accordingly, when a patient lays on their back, fluid (e.g., urine) may aggregate near the opening 306 against the skin of the subject. The fluid may be removed from the chamber 304 via the conduit 108. The conduit 108 may be disposed within wicking material and includes the inlet positioned within the fluid collection device and an outlet configured to be in fluid communication with one or more of a vacuum source or fluid storage container.

In some examples, the vacuum source (not shown) may be remotely located from the cup portion 352. In such examples, the conduit 108 may extend out of and away from the cup portion 352 to the vacuum source or a fluid storage container. For example, the inlet 110 of the conduit may be used to remove fluid from the chamber 304 via vacuum when an outlet (not shown) of the conduit 108 is in fluid communication with the vacuum source of fluid storage container.

The outlet (not shown) may be in fluid communication with a fluid storage container (not shown) through the conduit 108 in the direction shown by the arrows. The fluid impermeable barrier 302 may include at least one aperture 324 that is sized and shaped to receive and seal against the conduit 108, such as within the chamber 304. Accordingly, the interior region of the chamber 304 may be in fluid communication with the vacuum source via the conduit 108. As the vacuum source applies a vacuum/suction in the direction of the arrows in FIG. 3, the fluid in the chamber 304 may be removed through the conduit 108. In some examples, the fluid may be pumped through the vacuum source into a section of the conduit 108 in fluid communication with a fluid storage container (not shown) into which the fluid may be deposited.

In some examples, portions of the chamber 304 may be substantially empty due to the varying sizes and rigidity of the male penis. However, in some examples (not shown), the outermost regions of the chamber 304 (e.g., periphery of the interior regions of the cup portion 352) can include a porous material (e.g., one or more of the fluid permeable membrane 118 and fluid permeable support 120, FIG. 2B) configured to blunt a stream of urine from the male urethra thereby limiting splashing and/or to direct the fluids to a selected region of the chamber 304. Since the chamber 304 is substantially empty (e.g., substantially all of the chamber 304 forms a reservoir), the fluids are likely to pool at a gravimetrically low point of the chamber 304. The gravimetrically low point of the chamber 304 can be at an intersection of the garment against the skin of the individual or the skin of an individual and the fluid collection device 300 (proximate to opening 356), a corner formed in the cup portion 352, or another suitable location (e.g., proximate to a region opposite the opening 356). The inlet 110 of the conduit 108 can be positioned to be adjacent or proximate to the gravimetrically low point of the chamber 304.

During operation, a male using the fluid collection device 300 can discharge fluids (e.g., urine) into the chamber 304. The fluids can pool or otherwise be collected in the chamber 304, such as against the skin of the user (e.g., wearer). At least some of the fluids can enter the interior of the conduit 108 via the inlet 110. The fluid may be drawn out of the fluid collection device 300 via the vacuum/suction provided by the vacuum source. In some examples, during operation, the passageway 362 may substantially maintain the pressure in the chamber 304 at atmospheric pressure even though fluid is introduced into and subsequently removed from the chamber 304.

Figure 4:
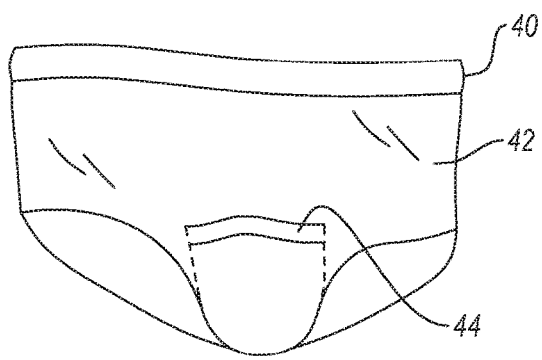
FIG. 4 is a front view of a garment for fluid collection, according to an embodiment.

FIG. 4 is a front view of a garment 40 for fluid collection, according to an embodiment. The garment 40 may be similar or identical to the garment 10 in one or more aspects. The garment 40 includes a fabric body 42 that is sized and shaped to fit on a pelvis of a wearer and maintain position thereon. The fabric body 42 may be sized, shaped, and configured to form undergarments in the form of briefs. The fabric body 42 of the garment 40 may be similar or identical to the fabric body 12 in one or more aspects. The fabric body 42 of the garment 40 includes a port 44 therein. The port 44 of the garment 40 may be similar or identical to the port 14 in one or more aspects. For example, the port 44 may be positioned in the crotch of the fabric body 42. The port 44 is positioned on or over the region of the urethra of the wearer (e.g., within the region of the crotch) when the garment 40 is worn. A fluid collection device (e.g., 100 or 300) may be disposed within the port 44, such that fluids in the region (e.g., urine) may be collected by the fluid collection device. Accordingly, the garment 40 and port 44 thereon may serve to align the fluid collection device with the urethra of the user such that fluids originating therefrom can be collected before soiling clothing or bedding.

Figure 4A:
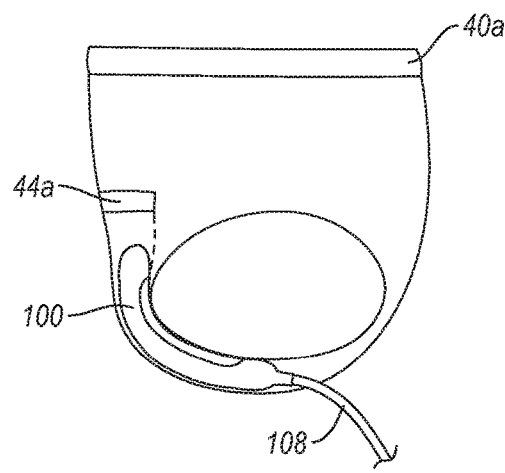
FIG. 4A is a side view schematic of the garment of FIG. 4, according to an embodiment.

FIG. 4A is a side view schematic of the garment of FIG. 4, according to an embodiment. FIG. 4A depicts the garment 40a, which includes port 44a which contains female fluid collection device therein, such as fluid collection device 100. The fluid collection device 100 is sized and shaped to fit within the port 44a. The port 44a is sized, positioned, and shaped to locate the fluid collection device 100 on or over the urethra of a female wearing the garment 40a. For example, the port 44a can be sized and positioned to receive the fluid collection device 100 and locate the opening (not shown) of the fluid collection device on the urethral region or opening of the wearer of the garment 40a. The port 44a may be complementary in size to the fluid collection device 100, such as to retain the fluid collection device in a substantially fixed position within the garment 40a. As shown, port 44a may extend from a pubic region to a perineal region. The port 44a may be disposed in or on the garment 40a. The port 44a may include enough fabric to allow the fluid collection device 100 to be inserted therein and limit movement of the fluid collection device 100 within the port 44a and garment 40a when inserted. In some examples, the port 44a can be adjustable, such as having one or more adjustable straps to adjust the volume of space within the port 44a to retain the fluid collection device 100 or allow a larger fluid collection device to be inserted therein.

The port 44a may include one or more holes therein to pass the conduit 108 therethrough. For example, a hole may be formed in the garment 40a in a lower portion of the port 44a (e.g., perineal region) to allow the conduit 108 to be disposed on a lowermost portion of the fluid collection device 100 when in use (e.g., when worn). The conduit 108 may be inserted into the fluid collection device 100 within the port 44a. The garment 40a may be worn by a female user to contain and remove fluid emissions. Similar garments can be used to treat male wearers (e.g., users).

Figure 4B:
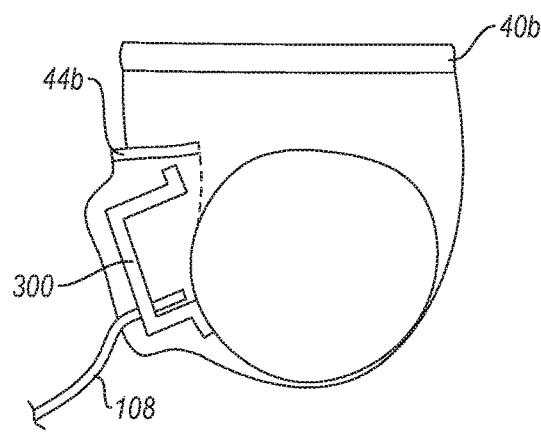
FIG. 4B is a side view schematic of the garment of FIG. 4, according to an embodiment.

FIG. 4B is a side view schematic of the garment of FIG. 4, according to an embodiment. FIG. 4B depicts the garment 40b, which includes port 44b which contains a male fluid collection device therein, such as fluid collection device 300. The fluid collection device 300 is sized and shaped to fit within the port 44b. The port 44b is sized, positioned, and shaped to locate the fluid collection device 300 on or over the urethra of a male wearing the garment 40b. For example, the port 44b can be sized and positioned to receive the fluid collection device 300 and locate the cup portion (FIG. 3) of the fluid collection device 300 over (e.g., on) the urethral region or opening (e.g., penis) of the wearer of the garment 40b. The port 44b may be complementary in size to the fluid collection device 300, such as to retain the fluid collection device 300 in a substantially fixed position within the garment 40b. As shown, port 44b may extend from a pubic region towards a perineal region. The port 44b may be disposed in or on the garment 40b. The port 44b may include enough fabric to allow the fluid collection device 300 to be inserted therein and limit movement of the fluid collection device 300 within the port 44b and garment 40b when inserted. In some examples, the port 44b can be adjustable, such as having one or more adjustable straps to adjust the volume of space within the port 44b to retain the fluid collection device 300 or allow a larger fluid collection device to be inserted therein.

The port 44b may include one or more holes therein to pass the conduit 108 therethrough. For example, a hole may be formed in the garment 40b in a lower portion of the port 44b to allow the conduit 108 to be disposed on a lowermost portion of the fluid collection device 300 when in worn. The conduit 108 may be inserted into the fluid collection device 300 within the port 44b. The garment 40b may be worn by a male user to contain and remove fluid emissions.

In some examples, one or more of the port or the fabric body may include a stretchable material. The stretchable material may accommodate the fluid collection device and retain the same within the port.

Figure 4C:
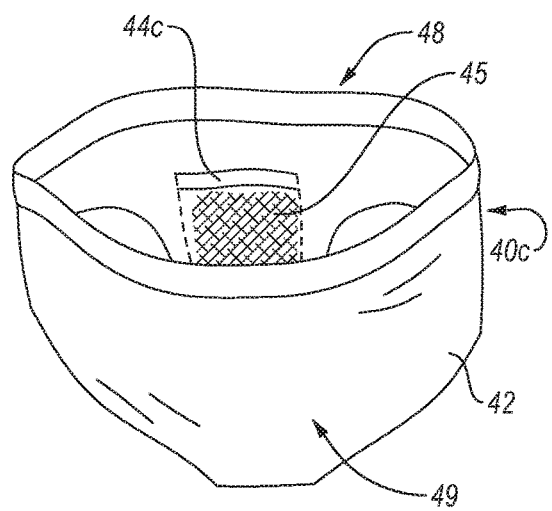
FIG. 4C is an isometric view of the back of the garment of FIG. 4, according to an embodiment

In some examples, the garment can include a porous material to allow fluids to pass from the wearer into the fluid collection device therein. FIG. 4C is an isometric view of the back of the garment of FIG. 4, according to an embodiment. FIG. 4C depicts the garment 40c from the back 49. The garment 40c includes fabric body 42 with a port 44c to contain a fluid collection device therein, such as fluid collection device 100 or 300. The port 44c is sized, positioned, and shaped to locate the fluid collection device on or over the urethra of a user wearing the garment 40c. For example, the port 44c can be sized and positioned to receive the fluid collection device and locate an opening of the fluid collection device over (e.g., on) the urethral region or opening of the wearer of the garment 40c. The port 44c may be complementary in size to the fluid collection device, such as to retain the fluid collection device in a substantially fixed position within the garment 40c. As shown, port 44c may be located on an interior of the garment 40c. FIG. 4C shows the interior of the garment 40c including the port 44c located in the front 48 of the garment 40c such as in an interior pubic region of the garment 40c. The port 44c can include a porous material 45 in a region positioned to be located between the skin of the wearer and the fluid collection device. The porous material 45 may allow fluid to flow from the wearer to into the fluid collection device within the port 44c with minimal absorption by the garment 40c (e.g., the material of the port). In some examples, the porous material 45 includes a hydrophobic or non-absorbent material, such as polypropylene, polyester, acrylic fibers, etc. In some examples, the porous material 45 includes a fabric mesh, such as cotton, wool, silk, rubber, polyester, acrylic fibers, any fabric disclosed herein, etc., mesh. For example, the garment 40c may include a mesh material or non-absorbent material in a position to contact the subject and the opening of the fluid collection device.

In some examples, the fabric body 42 can be made of one or more of a fabric mesh, hydrophobic material, or non-absorbent material. In such examples, the port may be made of the same material or a different material than the fabric body, such as any of the materials for a fabric body disclosed herein. In such examples, the port may include a port body (e.g., piece of fabric forming a pocket) affixed to the outer surface of the fabric body to form a pocket between the fabric body and the port body. Fluids emitted by the wearer can pass through the fabric body 42 and into the fluid collection device with minimal absorption by the fabric body.

In some examples, the porous material 45 may be stretchable or have and excess of material to allow a penis of a male wearer to fit into the chamber of a fluid collection device disposed in the port. In some examples (not shown), the porous material 45 or fabric body 42 may include a hole in the port rejoin sized and shaped for allowing the penis of a male user to be inserted into the chamber of the fluid collection device disposed in the port.

In some examples, the garment may include one or more holes or perforations in the fabric in the urethral region of the garment (e.g., region that fits over the urethra of the wearer). In such examples, fluid passes through the one or more holes or perforations in the fabric into the fluid collection device. The opening of the fluid collection device may be located at the one or more holes or perforations.

The garments herein may have different forms including pants; shorts; undergarments such as briefs, boxer briefs, a thong, a jock strap, etc.; a sanitary belt; or the like.

Figure 5:
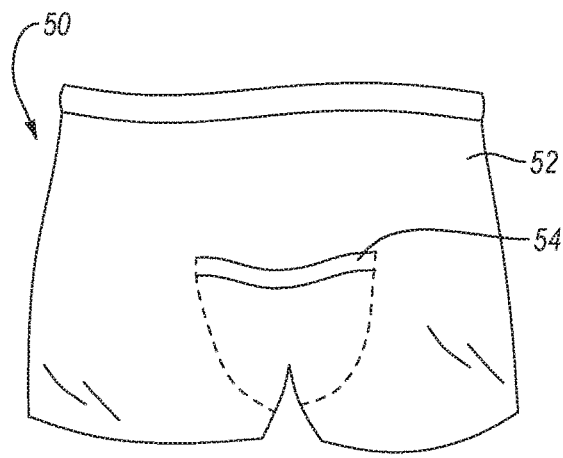
FIGS. 5-7 are front views of garments for fluid collection, according to embodiments.

FIG. 5 is a front view of a garment 50 for fluid collection, according to an embodiment. The garment 50 may be similar or identical to the garment 10 in one or more aspects. The garment 50 includes a includes a fabric body 52 that is sized and shaped to fit on a pelvis of a wearer and maintain position thereon. The fabric body 52 may be sized, shaped, and configured to form undergarments in the form of boxer briefs or shorts. The fabric body 52 of the garment 50 may be similar or identical to the fabric body 12 in one or more aspects. The fabric body 52 of the garment 50 includes a port 54 therein. The port 54 of the garment 50 may be similar or identical to the port 14 in one or more aspects. For example, the port 54 may be positioned in the crotch of the fabric body 52. The port 54 is positioned over the region of the urethra of the wearer (e.g., within the region of the crotch) when the garment 50 is worn. A fluid collection device (e.g., 100 or 300) may be disposed within the port 54, such that fluids in the region (e.g., urine) may be collected by the fluid collection device. Accordingly, the garment 50 and port 54 thereon may serve to align the fluid collection device with the urethra of the user such that fluids originating therefrom can be collected before soiling clothing or bedding.

Figure 6:
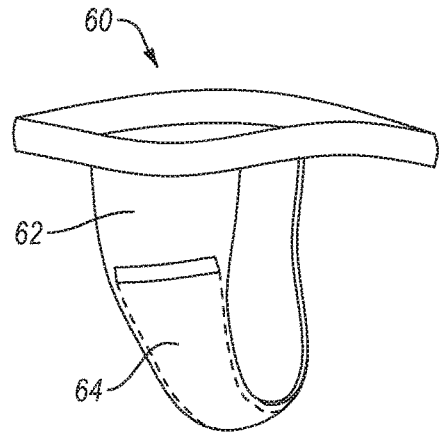

FIG. 6 is a front view of a garment 60 for fluid collection, according to an embodiment. The garment 60 may be similar or identical to the garment 10 in one or more aspects. The garment 60 includes a includes a fabric body 62 that is sized and shaped to fit on a pelvis of a wearer and maintain position thereon. The fabric body 62 may be sized, shaped, and configured to form undergarments in the form of thong underwear. The fabric body 62 of the garment 60 may be similar or identical to the fabric body 12 in one or more aspects. The fabric body 62 of the garment 60 includes a port 64 therein. The port 64 of the garment 60 may be similar or identical to the port 14 in one or more aspects. For example, the port 64 may be positioned in the crotch of the fabric body 62. The port 64 is positioned over the region of the urethra of the wearer (e.g., within the region of the crotch) when the garment 60 is worn. A fluid collection device (e.g., 100 or 300) may be disposed within the port 64, such that fluids in the region (e.g., urine) may be collected by the fluid collection device. Accordingly, the garment 60 and port 64 thereon may serve to align the fluid collection device with the urethra of the user such that fluids originating therefrom can be collected before soiling clothing or bedding.

Figure 7:
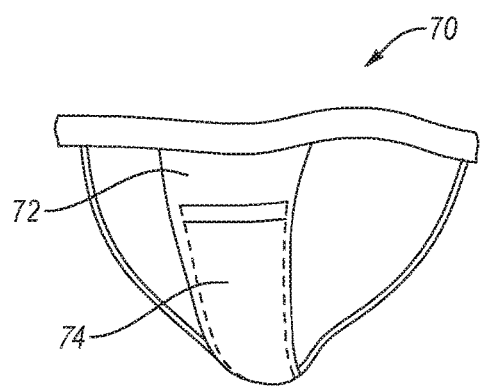

FIG. 7 is a front view of a garment 70 for fluid collection, according to an embodiment. The garment 70 may be similar or identical to the garment 10 in one or more aspects. The garment 70 includes a includes a fabric body 72 that is sized and shaped to fit on a pelvis of a wearer and maintain position thereon. The fabric body 72 may be sized, shaped, and configured to form undergarments in the form of a jock strap. The fabric body 72 of the garment 70 may be similar or identical to the fabric body 12 in one or more aspects. The fabric body 72 of the garment 70 includes a port 74 therein.

The port 74 of the garment 70 may be similar or identical to the port 14 in one or more aspects. For example, the port 74 may be positioned in the crotch of the fabric body 72. The port 74 is positioned over the region of the urethra of the wearer (e.g., within the region of the crotch) when the garment 70 is worn. A fluid collection device (e.g., 100 or 300) may be disposed within the port 74, such that fluids in the region (e.g., urine) may be collected by the fluid collection device. Accordingly, the garment 70 and port 74 thereon may serve to align the fluid collection device with the urethra of the user such that fluids originating therefrom can be collected before soiling clothing or bedding.

Figure 7A:
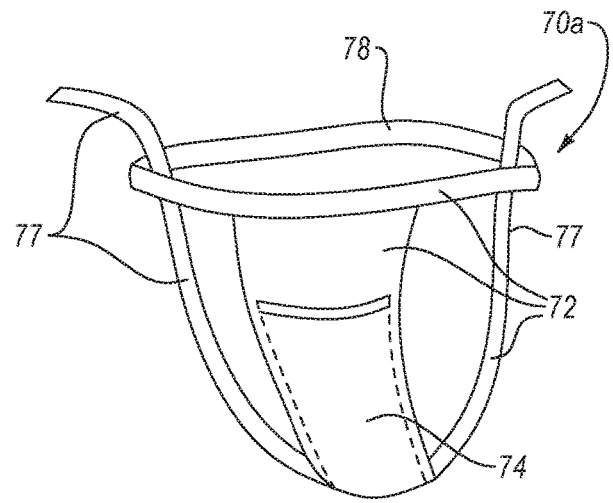
FIG. 7A is a front view of a garment for fluid collection, according to an embodiment.

In some examples, the garment may be adjustable to adjust the position of the port with respect to the urethral region of the wearer. For example, the garment may include one or more adjustable straps. FIG. 7A is a front view of a garment 70a for fluid collection, according to an embodiment. The garment 70a may be similar or identical to the garment 10 in one or more aspects. The garment 70a includes a includes a fabric body 72a that is sized and shaped to fit on a pelvis of a wearer and maintain position thereon. The fabric body 72a may be sized, shaped, and configured to form undergarments generally in the form of a jock strap. The fabric body 72a of the garment 70 may be similar or identical to the fabric body 12 in one or more aspects. The fabric body 72a of the garment 70 includes a port 74 therein. The port 74 of the garment 70a may be similar or identical to the port 14 in one or more aspects. For example, the port 74 may be positioned in the crotch of the fabric body 72a. The port 74 is positioned over the region of the urethra of the wearer (e.g., within the region of the crotch) when the garment 70a is worn. The fabric body 72a may include one or more adjustable straps 77 and a waistband 78. The one or more adjustable straps may attach to the port 74 and the waistband 78. The waistband 78 and the one or more adjustable straps 77 may have complementary connections (e.g., button and button holes, hook and loop strips, etc.). The adjustable straps 77 may include multiple connection features (e.g., multiple buttons, hook and loop strips, etc.) along the body of the strap to allow adjustment of the length of the adjustable straps between the waistband 78 and the port 74. In some examples, the waist band 78 may be expandable or contractible. A fluid collection device (e.g., 100 or 300) may be disposed within the port 74, such that fluids in the region (e.g., urine) may be collected by the fluid collection device. The adjustable straps 77 may be used to change the location of the fluid collection device with the urethral region of the wearer. Accordingly, the garment 70, adjustable straps 77, and port 74 may serve to align the fluid collection device with the urethra of the user such that fluids originating therefrom can be collected before soiling clothing or bedding.

Any of the garments disclosed herein may be adjustable in one or more dimensions to selectively adjust the position of the port and fluid collection device therein with respect to a urethral region of the wearer. Accordingly, a single garment may be used for a wide variety of sizes of users.

In some examples (not shown), the garment may include a structure analogous to a sanitary belt wherein a pocket or port (and fluid collection device) is held in position over the urethra of the wearer between opposing connections of the sanitary belt.

Figure 8:
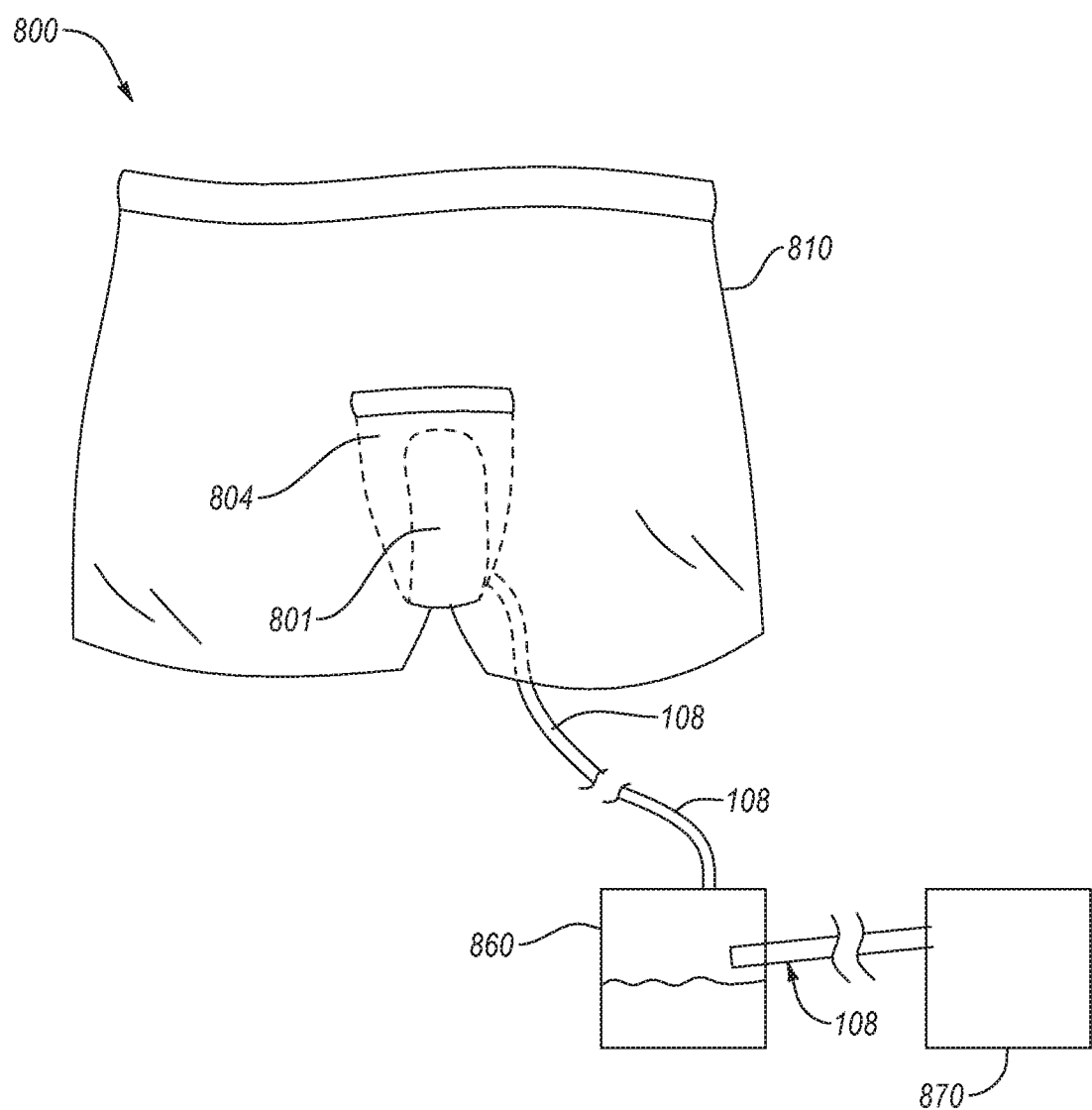
FIG. 8 is a block diagram of a system for fluid collection, according to an embodiment

FIG. 8 is a block diagram of a system 800 for fluid collection, according to an embodiment. The system 800 includes a garment 810 containing a fluid collection device 801 in a port 814 thereon, a fluid storage container 860, and a vacuum source 870. The fluid collection device 801, the fluid storage container 860, and the vacuum source 870 may be in fluid communication with each other via one or more conduits 108. For example, fluid collection device 801 may be operably coupled to (e.g., in fluid communication with) one or more of the fluid storage container 860 or the portable source 870 via the conduits 108. The garment 810 may be similar or identical to any of the garments disclosed herein. The fluid collection device 801 may be similar or identical to any of the fluid collection devices disclosed herein, such as a male or female fluid collection device.

Fluid (e.g., urine or other bodily fluids) collected in the fluid collection device 801 may be removed from the fluid collection device 801 via the conduit 108 which protrudes into an interior region of the fluid collection device 801. For example, a first open end of the conduit 108 may extend into the fluid collection device 801 to a reservoir therein. The second open end of the conduit 108 may extend into the fluid collection device 801 or the vacuum source 870. The suction force may be introduced into the interior region of the fluid collection device 801 via the first open end of the conduit 108 responsive to a suction (e.g., vacuum) force applied at the second end of the conduit 108. The suction force may be applied to the second open end of the conduit 108 by the vacuum source 870 either directly or indirectly.

The suction force may be applied indirectly via the fluid storage container 860. For example, the second open end of the conduit 108 may be disposed within the fluid storage container 860 and an additional conduit 108 may extend from the fluid storage container 860 to the vacuum source 870. Accordingly, the vacuum source 870 may apply suction to the fluid collection device 801 via the fluid storage container 860. In some examples, the suction force may be applied directly via the vacuum source 870. For example, the first open end of the conduit 108 may be disposed in the fluid collection device 801 and the second open end of the conduit 108 may be disposed within the vacuum source 870. An additional conduit 108 may extend from the vacuum source 870 to a point outside of the fluid collection device 801, such as to the fluid storage container 860. In such examples, the vacuum source 870 may be disposed between the fluid collection device 801 and the fluid storage container 860.

In examples, the fluid storage container 860 may include a bag (e.g., drainage bag), a bottle or cup (e.g., collection jar), tubing, or any other container for storing bodily fluids such as urine. In examples, the conduit 108 may extend from the fluid collection device 801 and attach to the fluid storage container 860 at a first point therein. An additional conduit 108 may attach to the fluid storage container 860 at a second point thereon and may extend and attach to the vacuum source 870. For example, the fluid storage container 860 may include a container in fluid communication with a first conduit section that is also in fluid communication with the fluid collection device 801. The container may be in fluid communication with a second section of the conduit 108 that is also in fluid communication with the vacuum source. In such examples, the vacuum source 870 may provide a vacuum/suction through the container to the fluid collection device 801 to provide suction in the chamber of the fluid collection device. Accordingly, a vacuum (e.g., suction) may be drawn through fluid collection device 801 via the fluid storage container 860. As the fluid is drained from the chamber, the fluid may travel through the first section of conduit to the fluid storage container where it may be retained. Fluid, such as urine, may be drained from the fluid collection device 801 using the vacuum source 870.

The vacuum source 870 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 870 may provide a vacuum or suction to remove fluid from the fluid collection device 801. In examples, the vacuum source 870 may be powered by one or more of a power cord (e.g., connected to a power socket), one or more batteries, or even manual power (e.g., a hand operated vacuum pump). The vacuum sources 870 disclosed herein may include one or more of a switch, a button, a plug, a remote, or any other device suitable to activate the vacuum source 870.

Figure 9:
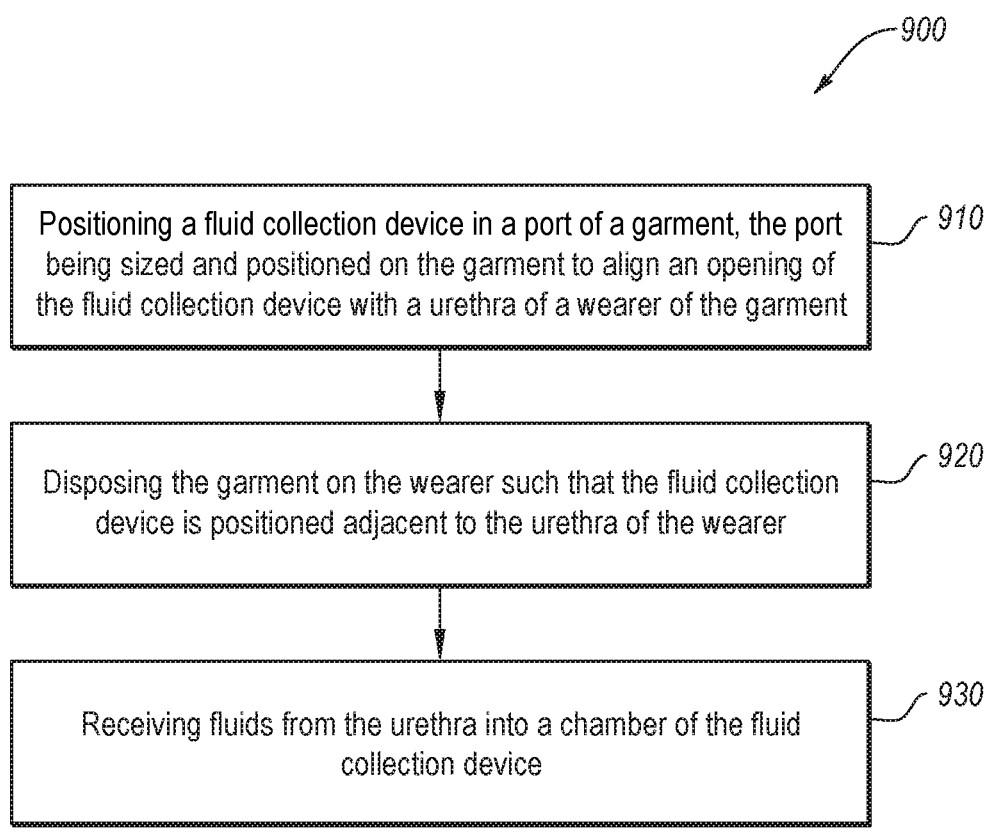
FIG. 9 is a flow diagram of a method to collect fluid, according to an embodiment.

FIG. 9 is a flow diagram of a method 900 to collect fluid, according to an embodiment. The method 900 can include act 910, which recites "positioning a fluid collection device in a port of a garment, the port being sized and positioned on the garment to align an opening of the fluid collection device with a urethra of a wearer of the garment." Act 910 may be followed by act 920, which recites "disposing the garment on the wearer such that the fluid collection device is positioned adjacent to the urethra of the wearer." Act 920 may be followed by act 930, which recites "receiving fluids from the urethra into a chamber of the fluid collection device."

Acts 910, 920, 930 of the method 900 are for illustrative purposes. For example, the act 910, 920, 930 of the method 900 can be performed in different orders, split into multiple acts, modified, supplemented, or combined. In an example, one or more of the acts 910, 920, 930 of the method 900 can be omitted from the method 900. For example, the method 900 may not include the act 910. Any of the acts 910, 920, or 930 can include using any of the garments, fluid collection devices, vacuum sources, fluid storage containers, systems, or components of the same disclosed herein. For example, the fluid collection device may include a fluid impermeable barrier at least partially defining the chamber, the fluid impermeable barrier also defining an opening extending therethrough, the opening configured to be positioned adjacent to a female urethra or have a male urethra positioned therethrough. The fluid collection device may include a wicking material disposed with the chamber and a conduit disposed within wicking material, the conduit including an inlet positioned within the fluid collection device and an outlet.

Act 910 recites "positioning a fluid collection device in a port of a garment, the port being sized and positioned on the garment to align an opening of the fluid collection device with a urethra of a wearer of the garment." In some examples, act 910 includes inserting a fluid collection device in a port of a garment. The fluid collection device may be a female fluid collection device and the garment may include a port configured to retain the female fluid collection device therein. The fluid collection device may be a male fluid collection device and the garment may include a port configured to retain the male fluid collection device therein. The port may be positioned on the garment according to the sex of the intended wearer.

Act 920 recites, "disposing the garment on the wearer such that the fluid collection device is positioned adjacent to the urethra of the wearer." Disposing the garment on the wearer such that the fluid collection device is positioned adjacent to the urethra of the wearer can include donning the garment or placing the garment on the wearer prior to, after, or contemporaneously with positioning a fluid collection device in a port of a garment. Disposing the garment on the wearer such that the fluid collection device is positioned adjacent to the urethra of the wearer may include disposing the garment on the wearer such that the fluid collection device is positioned adjacent to the urethra of the wearer when the fluid collection device is positioned therein. For example, disposing the garment on the wearer such that the fluid collection device is positioned adjacent to the urethra of the wearer may be performed prior to act 910. Disposing the garment on the wearer such that the fluid collection device is positioned adjacent to the urethra of the wearer can include donning or placing any of the garments disclosed herein on the wearer. For example, disposing the garment on the wearer such that the fluid collection device is positioned adjacent to the urethra of the wearer may include adjusting one or more dimensions of the garment with adjustable straps thereon to place the port or the fluid collection device thereon over the urethra of the wearer.

In some examples, disposing the garment on the wearer such that the fluid collection device is positioned adjacent to the urethra of the wearer can include positioning the opening of a female fluid collection device such that the fluid permeable membrane of the female fluid collection device abuts or is positioned proximate to the female urethra. For example, positioning an opening of a fluid collection device adjacent to a female urethra of a user may include positioning opening of the fluid collection device, within the port of the garment, on or between the labia of a wearer.

Act 930 recites "receiving fluids from the urethra into a chamber of the fluid collection device." For example, act 930 can include wicking the fluids away from urethra via the opening using wicking material (e.g., fluid permeable membrane and a fluid permeable support). In some examples, act 930 can include receiving the fluids into the chamber of the fluid collection device. In either example, act 930 can include flowing the fluid towards a portion of the chamber that is in fluid communication with an inlet of a conduit in fluid communication a vacuum source. For instance, act 930 can include flowing the fluids to a substantially unoccupied portion of the chamber (e.g., a reservoir), to a gravimetrically low point of the chamber, etc.

The method 900 may include applying suction with a vacuum source effective to suction the fluids from the chamber via a conduit disposed therein that is in fluid communication with the vacuum source. In examples, applying suction with a vacuum source effective to suction the fluids from the chamber via a conduit disposed therein that is in fluid communication with the vacuum source can include using any of the vacuum sources disclosed herein. In an example, applying suction can include activating the vacuum source (e.g., suction device) in fluid communication with the inlet of the conduit in the fluid collection device. In examples, activating the vacuum source in fluid communication with the inlet of the conduit in the fluid collection device can include supplying power to the vacuum source by one or more of flipping an on/off switch, pressing a button, plugging the vacuum source into a power outlet, putting batteries into the vacuum source, etc. In examples, the vacuum source may include a hand operated vacuum pump and applying suction with a vacuum source may include manually operating the hand operated vacuum pump effective to suction the fluids from the chamber via the conduit disposed therein that is in fluid communication with the vacuum source.

In examples, applying suction with a vacuum source effective to suction the fluids from the chamber via a conduit disposed therein that is in fluid communication with the vacuum source can be effective to remove at least some fluid (e.g., urine) from the chamber (e.g., interior region) of the fluid collection device. In examples, applying suction with a vacuum source effective to suction the fluids from the chamber via a conduit disposed therein that is in fluid communication with the vacuum source can be effective to transfer at least some of the fluid from the chamber of the fluid collection device to a fluid storage container (e.g., a bottle or bag) in fluid communication with the vacuum source and the fluid collection device. In examples, the vacuum source may be spaced from the fluid collection device.

In examples, applying suction with a vacuum source effective to suction the fluids from the chamber via a conduit disposed therein that is in fluid communication with the vacuum source may include detecting moisture in the chamber (e.g., via one or more moisture sensors) and responsive thereto, activating the vacuum source to provide suction in the chamber. Control of the vacuum source responsive to the signals indicating that moisture or a threshold level thereof is present in the chamber can be automatic, such as via a controller, or may merely provide an indication that a level of moisture is present that may necessitate removal of fluid from the chamber of the fluid collection device. In the latter case, a user may receive the indication and activate the vacuum pump.

In an example, the method 900 can include collecting the fluids that are removed from the fluid collection device, such as into a fluid storage container that is spaced from the fluid collection device that is in fluid communication with the conduit. The fluid storage container can include any of the fluid storage containers disclosed herein.

Devices and methods described herein can be configured to collect urine from a male user, such as having a fluid collection device shaped and sized to receive a male urethra (e.g., penis) therein. In examples, the method 900 can include positioning a receptacle of a male fluid collection device around the male urethra such that the male urethra is positioned in the receptacle. In such an example, the method 900 can include positioning a cup portion of the male fluid collection device in a hollowed region of the receptacle such that the male urethra is positioned through an opening of the cup portion of the male fluid collection device.

While various aspects and embodiments have been disclosed herein, other aspects and embodiments are contemplated. The various aspects and embodiment disclosed herein are for purposes of illustration and are not intended to be limiting.

We claim:

1. A urine collection assembly, comprising:
 a wearable garment including at least a waistband having a front region and a rear region, and two elongated straps each having a first end region secured to the rear region of the waistband and a second end region distal to the first end region, the two elongated straps angling away from each other between the second end region and the first end region such that the two elongated straps at least partially define an opening in the wearable garment between the two elongated straps and at least partially between rear regions of the waistband and the first end region of the two straps; and
 a urine collection device releasably securable to a portion of the wearable garment, the urine collection device having a top region disposed at least proximate to the front region of the waistband and a bottom region disposed at least proximate to the second end region of each of the two elongated straps when the urine collection device is releasably secured to the portion of the wearable garment, the urine collection device including:
   a first member having an aperture and including a channel in fluid communication with a suction outlet configured to provide fluid communication with a vacuum source;
   a fluid permeable layer disposed external to the first member;
   a fabric layer that at least partially covers the first member and the fluid permeable layer, at least a portion of the fabric layer being positioned on the urine collection device to define an outermost region of a portion of the urine collection device that directly receives urine discharged by a user; and
   a reservoir positioned within the urine collection assembly and in fluid communication with the channel.

2. The urine collection assembly of claim 1, wherein the reservoir is a substantially unoccupied area that is void of other materials.

3. The urine collection assembly of claim 1, further comprising a fluid impermeable outer layer.

4. The urine collection assembly of claim 3, wherein:
 the fluid impermeable outer layer forms a cylinder to define a chamber there within, and further comprises a first opening for the suction outlet to attach thereto and a separate second elongated opening positioned to enable fluids to enter the chamber through the second elongated opening from outside of the fluid collection device;
 the fluid permeable layer is substantially cylindrical and positioned within the chamber such that the fluid impermeable outer layer and the fluid permeable layer are at least partially concentric with one another; and
 the fabric layer extends across the elongated opening and positioned at least partially between the fluid permeable layer and the fluid impermeable outer layer.

5. The urine collection device of claim 3, wherein the fluid impermeable outer layer defines at least a portion of the reservoir.

6. The urine collection assembly of claim 1, wherein the aperture of the first member is disposed adjacent to the reservoir.

7. A urine collection assembly, comprising:
 a wearable garment including at least a waistband having a front region and a rear region, and two elongated straps each having a first end region secured to the rear region of the waistband and a second end region distal to the first end region, the two elongated straps angling away from each other between the second end region and the first end region such that the two elongated straps at least partially define an opening in the wearable garment between the two elongated straps and at least partially between rear regions of the waistband and the first end region of the two straps; and
 a urine collection device releasably securable to a portion of the wearable garment and having a top region disposed at least proximate to the front region of the waistband and a bottom region disposed at least proximate to the second end region of the two elongated straps when the urine collection device is releasably secured to the portion of the wearable garment, the urine collection device including:
   a first layer at least partially defining a reservoir in the urine collection device and defining an opening configured to receive urine therethrough, the first layer including a material that substantially prevents the urine from exiting through the material;

an outlet in fluid communication with the reservoir and configured to provide fluid communication between a vacuum source and the reservoir;

a fluid permeable layer including at least a synthetic fiber; and a fabric layer at least partially adjacent to and covering the fluid permeable layer such that the fluid permeable layer is at least partially disposed between at least a portion of the fabric layer and at least a portion of the first layer, wherein at least a portion of the fabric layer is positioned on the urine collection device to define an outermost region of a portion of the urine collection device that directly receives the urine discharged by the user.

8. The urine collection assembly of claim 7, further comprising a channel extending between the outlet and the reservoir.

9. The urine collection assembly of claim 7, wherein the reservoir is a substantially unoccupied area that is void of other materials.

10. The urine collection assembly of claim 7, wherein:
the first layer is substantially cylindrical and the material of the first layer is fluid impermeable at least partially defining a chamber in fluid communication with the opening;
the fluid permeable layer is substantially cylindrical and positioned within the chamber; and
at least the portion of the fabric layer that is positioned on the urine collection device to directly receive the urine discharged by the user at least partially extends across the opening in the first layer and covers the fluid permeable layer.

11. A urine collection assembly, comprising:
a wearable garment including at least a waistband having a front region and a rear region, and two elongated straps each having a first end region secured to the rear region of the waistband and a second end region distal to the first end region, the two elongated straps angling away from each other between the second end region and the first end region such that the two elongated straps define an opening in the wearable garment between the two elongated straps and at least partially between rear regions of the waistband and the first end region of the two straps; and a urine collection device releasably securable to a portion of the wearable garment and having a top region disposed at least proximate to the front region of the waistband and a bottom region disposed at least proximate to the second end region of the two elongated straps when the urine collection device is releasably secured to the portion of the wearable garment, the urine collection device including:

a support core including a non-absorbent material having a plurality of urine-receiving pores, the support core including a channel providing fluid communication between a vacuum suction and a reservoir in the urine collection device; and a layer disposed externally with respect to the support core and at least partially covering the support core, the layer including at least a polyester fiber and positioned on the urine collection device to define an outermost region of a portion of the urine collection device that directly receives urine discharged by the user.

12. The urine collection assembly of claim 11, wherein the support core at least partially defines the reservoir.

13. The urine collection assembly of claim 11, wherein the reservoir is a substantially unoccupied area that is void of other materials.

14. The urine collection assembly of claim 11, wherein the layer is adjacent to at least a portion of the support core.

15. The urine collection assembly of claim 14, further comprising a fluid impermeable layer secured to the support core and the layer with the support core positioned between at least a portion of the fluid impermeable layer and at least a portion of the layer.

16. The urine collection assembly of claim 15, wherein:
the fluid impermeable layer is elongated and substantially cylindrical with at least a portion of the fluid impermeable layer sized to fit between legs of a female user, the fluid impermeable layer at least partially defining an opening positioned to be disposed proximate to a urethra of the female user and chamber in fluid communication with the opening;
the support core is positioned within the chamber and substantially cylindrical; and
the layer extends across at least a portion of the opening.

17. The urine collection assembly of claim 7, wherein the fluid permeable layer is positioned adjacent to the fabric layer.

18. The urine collection assembly of claim 1, wherein the opening in the wearable garment between the two elongated straps is disposed on the wearable garment such that at least a portion of a gluteal cleft of the user wearing the wearable garment remains uncovered.

19. The urine collection assembly of claim 7, wherein the opening in the wearable garment between the two elongated straps is disposed on the wearable garment such that at least a portion of a gluteal cleft of the user wearing the wearable garment remains uncovered.

20. The urine collection assembly of claim 11, wherein the opening in the wearable garment between the two elongated straps is disposed on the wearable garment such that at least a portion of a gluteal cleft of the user wearing the wearable garment remains uncovered.

* * * * *